United States Patent
Kobayashi et al.

(10) Patent No.: US 6,548,543 B1
(45) Date of Patent: Apr. 15, 2003

(54) REMEDIES OR PREVENTIVES CONTAINING CYCLOPENTENONE COMPOUNDS AS THE ACTIVE INGREDIENT

(75) Inventors: Eiji Kobayashi, Otsu (JP); Hiromu Ohnogi, Muko (JP); Hiroaki Sagawa, Kusatsu (JP); Takanari Tominaga, Otsu (JP); Eiji Nishiyama, Moriyama (JP); Nobuto Koyama, Uji (JP); Katsushige Ikai, Shiga (JP); Ikunoshin Kato, Uji (JP)

(73) Assignee: Takara Shuzo Co., Ltd., Kyoto (JP)

( * ) Notice: Subject to any disclaimer, the term of this patent is extended or adjusted under 35 U.S.C. 154(b) by 0 days.

(21) Appl. No.: 09/763,244

(22) PCT Filed: Aug. 10, 1999

(86) PCT No.: PCT/JP99/04323

§ 371 (c)(1),
(2), (4) Date: Feb. 20, 2001

(87) PCT Pub. No.: WO00/10560

PCT Pub. Date: Mar. 2, 2000

(30) Foreign Application Priority Data

Aug. 18, 1998 (JP) ............................ 10-231659

(51) Int. Cl.[7] .................. A61K 31/215; A61K 31/235

(52) U.S. Cl. .................... 514/530; 514/531; 514/532

(58) Field of Search .................. 514/530, 531, 514/532

(56) References Cited

U.S. PATENT DOCUMENTS 6,111,145 A * 8/2000 Kobayashi et al. ......... 568/379
6,136,854 A * 10/2000 Koyama et al. ............ 514/532

FOREIGN PATENT DOCUMENTS

| EP | 0 941 981 A1 | 9/1999 |
| EP | 0 976 717 A1 | 2/2000 |
| JP | 2-247151 A | 10/1990 |
| WO | WO 98/13328 A1 | 4/1998 |
| WO | 98 25593 | 6/1998 |
| WO | WO 98/40346 A1 | 9/1998 |

OTHER PUBLICATIONS

Santoro, "Antiviral activity of cyclopentenone prostanoids", *Elsevier Science LTD.*, (1997), vol. 5, No. 7, pp. 276–281.

* cited by examiner

Primary Examiner—Kevin E. Weddington
(74) Attorney, Agent, or Firm—Browdy and Neimark, P.L.L.C.

(57) ABSTRACT

Remedies or preventives for diseases with a need for immunoregulation, diseases with a need for inhibition of inflammation, diseases with a need for regulation of tumor necrosis factor production, diseases with a need for regulation of fungal growth, diseases with a need for regulation of cell adhesion or disease with a deed for induction of heat-shock protein, which contain as the active ingredient at least one compound selected from among cyclopentenone derivatives represented by general formula [I], optically active isomers and salts thereof, wherein $R_1$ and $R_2$ are the same or different and each represents hydrogen, an aliphatic group, an aromatic group or an aromatic aliphatic group.

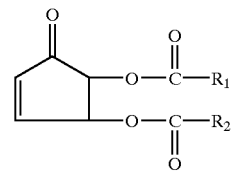

[I]

4 Claims, 8 Drawing Sheets

REMEDIES OR PREVENTIVES CONTAINING CYCLOPENTENONE COMPOUNDS AS THE ACTIVE INGREDIENT

REFERENCE TO RELATED APPLICATIONS

The present application is the national stage under 35 U.S.C. §371 of international application PCT/JP99/04323, filed Aug. 10, 1999 which designated the United States, and was not published in English.

TECHNICAL FIELD

The present invention relates to a pharmaceutical composition containing a cyclopentenone ester as an active ingredient.

BACKGROUND ART

Wide variety of drugs including alkylating agents, antimetabolites, carcinostatics such as vegetable alkaloids, antibiotics, immunoenhancers and immnoregulators are conventionally used for clinical therapies. However, pharmacotherapy using such drugs has not completed yet.

Among these, naturally occurring prostaglandins having α,β-unsaturated carbonyls in their five-membered rings, i.e., prostaglandins A and J, were reported to suppress DNA synthesis, suggesting their possible use as highly safe carcinostatics. Various derivatives thereof were synthesized (see JP-A 62-96438).

OBJECTS OF INVENTION

The main object of the present invention is to develop a cyclopentenone derivative having various physiological activities and to provide a pharmaceutical composition containing the compound as an active ingredient.

These and other objects as well as advantages of the present invention will be explained below in detail with reference to the attached drawings.

SUMMARY OF INVENTION

Figure 1:
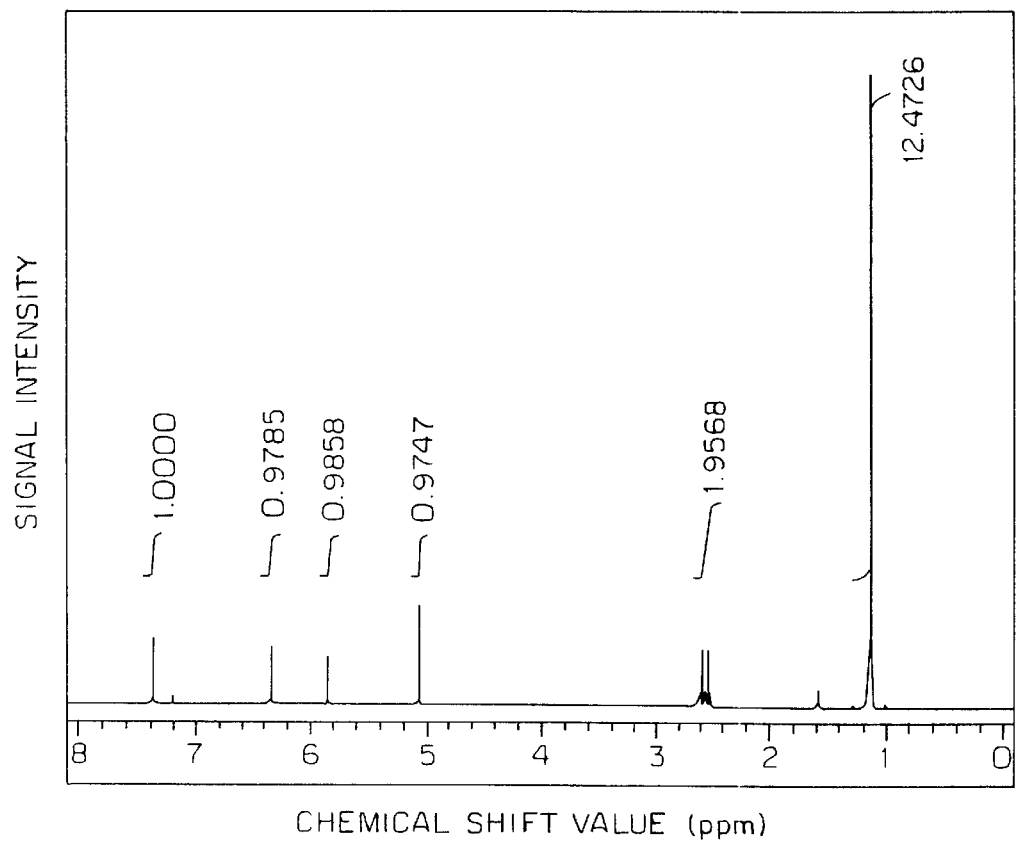
FIG. 1 illustrates the $^1$H-NMR spectrum of diisobutyrylcyclopentenone.

The present inventors have studied intensively in order to accomplish the objects and found that a cyclopentenone derivative of formula [I]:

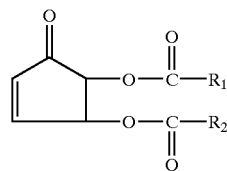

(wherein $R_1$ and $R_2$ may be identical or different each other, and are hydrogen, an aliphatic group, an aromatic group or an aromatic aliphatic group) is produced by reacting 4,5-dihydroxy-2-cyclopenten-1-one of formula [II] (hereinafter simply referred to as cyclopentenone):

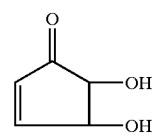

with a carboxylic acid and/or a reactive derivative thereof, and that the cyclopentenone derivative has strong physiological activities such as an immunoregulatory activity, an anti-inflammatory activity, an activity of inhibiting tumor necrosis factor production, an antifungal activity and an activity of inhibiting cell adhesion. Thus, the present invention has been completed.

Accordingly, the present invention provides a pharmaceutical composition which contains as an active ingredient at least one compound selected from the group consisting of a cyclopentenone derivative of formula [I] or an optical isomer thereof, and a salt thereof, said composition being used for treating or preventing a disease that requires immunoregulation for its treatment or prevention, a disease that requires suppression of inflammation for its treatment or prevention, a disease that requires inhibition of tumor necrosis factor production for its treatment or prevention, a disease that requires inhibition of a fungus for its treatment or prevention, a disease that requires inhibition of cell adhesion for its treatment or prevention, or a disease that requires induction of heat shock protein for its treatment or prevention.

DETAILED DESCRIPTION OF THE INVENTION

Cyclopentenones used in the present invention include isomers having hydroxyl groups at 4- and 5-positions configured in cis and isomers having the hydroxyl groups configured in trans. A cis or trans isomer of cyclopentenone or a mixture of the cis and trans isomers may be used in the present invention. Optical isomers thereof may also be used.

A cis isomer of cyclopentenone is obtained according to a chemical synthesis method [Helvetica Chimica Acta, 55:2838–2844 (1972)]. A trans isomer of cyclopentenone is obtained according to a chemical synthesis method [Carbohydrate Res., 247:217–222 (1993)] or by heating uronic acid (e.g., glucuronic acid), a uronic acid derivative (e.g., glucronolactone) or the like (see WO 98/13328). These heat treatment products containing cyclopentenone and products partially purified or purified therefrom can be used in the present invention.

For example, cyclopentenone is produced in a heat treatment product by heating a 1% solution of D-glucuronic acid as uronic acid at 121° C. for 4 hours. Cyclopentenone in the heat treatment product is extracted with a solvent. The extract is concentrated. The concentrate is then separated on silica gel column chromatography. Eluted fractions containing cyclopentenone are concentrated. Cyclopentenone is extracted from the concentrate with chloroform. The concentrated extract is subjected to normal phase column chromatography, thereby isolating cyclopentenone in the heat treatment product.

Optical isomers, (−)-4,5-dihydroxy-2-cyclopenten-1-one and (+)-4,5-dihydroxy-2-cyclopenten-1-one, can be obtained by optically resolving the thus isolated cyclopentenone. Of course, synthesized cyclopentenone can be optically resolved.

A cyclopentenone derivative of formula [I]:

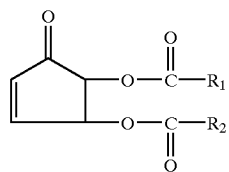

[I]

or an optical isomer thereof of the present invention is produced in a reaction mixture by simultaneously or sequentially reacting cyclopentenone and/or an optical isomer thereof with a carboxylic acid having hydrogen, an aliphatic group, an aromatic group or an aromatic aliphatic group and/or a reactive derivative thereof.

The following carboxylic acids having hydrogen, an aliphatic group, an aromatic group or an aromatic aliphatic group and corresponding to $R_1$ and $R_2$ in the cyclopentenone derivative of formula [I] or reactive derivatives thereof are used in the present invention.

Formic acid can be used as a carboxylic acid having hydrogen.

A carboxylic acid having an alkyl group and a carboxylic acid having an alkenyl group can be used as a carboxylic acid having an aliphatic group.

A carboxylic acid having a linear or branched alkyl group can be used as a carboxylic acid having an alkyl group. Although the length of the alkyl chain can be suitably selected depending on the biological activity, solubility or the like of the cyclopentenone derivative, a group of C1–30 is usually preferable. Examples of carboxylic acids having linear alkyl groups which can be used include acetic acid, propionic acid, butyric acid, valeric acid, hexanoic acid, heptanoic acid, n-octanoic acid, pelargonic acid, n-decanoic acid, undecanoic acid, lauric acid, tridecanoic acid, myristic acid, pentadecanoic acid, palmitic acid, heptadecanoic acid, stearic acid, nonadecanoic acid, icosanoic acid, behenic acid, lignoceric acid, cerotic acid and melissic acid.

Examples of carboxylic acids having branched alkyl groups which can be used include isobutyric acid, isovaleric acid, 2-methylbutyric acid, pivalic acid, 4-methylvaleric acid and 1,2-dimethylvaleric acid.

A carboxylic acid having a linear or branched alkenyl group can be used as a carboxylic acid having an alkenyl group. Although the chain length, the degree of unsaturation and the position of unsaturated bond of the alkenyl group can be suitably selected depending on the biological activity, solubility or the like of the cyclopentenone derivative, a group of C2–30 is usually preferable.

Examples of carboxylic acids having linear alkenyl groups which can be used include acrylic acid, vinylacetic acid, crotonic acid, isocrotonic acid, allylacetic acid, 2-hexenoic acid, 3-hexenoic acid, 3-octenoic acid, obtusilic acid, 10-undecenoic acid, palmitoleic acid, petroselinic acid, elaidic acid, oleic acid, linoleic acid, α-linolenic acid, γ-linolenic acid, eleostearic acid, icosatrienoic acid, arachidonic acid, eicosapentaenoic acid, brassidic acid, erucic acid, docosahexaenoic acid, ximenic acid and 21-triacontenoic acid.

Examples of carboxylic acids having branched alkenyl groups which can be used include methacrylic acid, tiglic acid, angelic acid and α-ethylcrotonic acid.

A carboxylic acid having an alkyl group that has a lower alkoxyl group of C1–4 as a substituent such as methoxyacetic acid can be used as a carboxylic acid having a substituted aliphatic group. A carboxylic acid having an alkenyl group that has a lower alkoxycarbonyl of C2–5 as a substituent such as methylmaleic acid can be used.

Examples of carboxylic acids having aromatic groups which can be used include benzoic acid, toluic acid, chlorobenzoic acid, bromobenzoic acid, nitrobenzoic acid, phthalic acid, isophthalic acid, terephthalic acid, salicylic acid, acetylsalicylic acid, acetylsalicylsalicylic acid, aminosalicylic acid, p-hydroxybenzoic acid, aminobenzoic acid, methoxybenzoic acid, acetamidobenzoic acid, vanillic acid, orsellinic acid, naphthoic acid, cinchomeronic acid, xanthurenic acid, quinic acid and kynureic acid. A carboxylic acid having an aromatic group used may be selected depending on the biological activity, solubility or the like of the cyclopentenone derivative to be produced.

Examples of carboxylic acids having aromatic aliphatic groups which can be used include phenylacetic acid, phenylpropionic acid, phenyllactic acid, phenylpyruvic acid, cinnamic acid, atropic acid and naphthylacetic acid. A carboxylic acid having an aromatic aliphatic group used may be selected depending on the biological activity, solubility or the like of the cyclopentenone derivative to be produced.

The aliphatic, aromatic or aromatic aliphatic group may have a substituent such as a functional group (e.g., an amino group, a nitro group, an oxo group, a hydroxyl group, a thiol group or a sulfate group) or a halogen (e.g., flourine, chlorine, bromine or iodine).

Thus, $R_1$ and $R_2$ in formula [I] may be identical or different each other, and examples thereof include hydrogen, a linear or branched C1–30 alkyl group, a linear or branched C2–30 alkenyl group, a C6–10 aryl group and a C1–30 alkyl C6–10 aryl group. They may be optionally substituted with at least one substituent selected from the group consisting of a C1–30 alkyl group, a C1–4 alkoxy group, a C2–5 alkoxycarbonyl group, an amino group, a nitro group, an oxo group, a hydroxyl group, a thiol group, a sulfate group and a halogen (e.g., flourine, chlorine, bromine or iodine).

Reactive derivatives of carboxylic acids are exemplified by an acid halide, an acid anhydride, an acid ester and a salt. A reactive derivative of the carboxylic acid to be used may be produced depending on the objects.

The reaction between a carboxylic acid or a reactive derivative thereof and cyclopentenone may be carried out such that $R_1$ and $R_2$ in the cyclopentenone derivative become identical or different each other.

Specifically, carboxylic acids having different groups for $R_1$ and $R_2$ may be simultaneously reacted with cyclopentenone. Alternatively, they may be reacted sequentially. In the latter case, a cyclopentenone derivative in which $R_1$ and $R_2$ are different each other can be efficiently produced by protecting one of the hydroxyl groups of cyclopentenone.

A cyclopentenone derivative or an optical isomer thereof produced by reacting cyclopentenone or an optical isomer thereof with carboxylic acid has an immunoregulatory activity, an anti-inflammatory activity, an activity of inhibiting tumor necrosis factor production, an antifungal activity, an activity of inhibiting cell adhesion or the like. The cyclopentenone derivative or an optical isomer thereof can be purified and isolated from the reaction mixture using one of these activities as an index. Known purification/isolation means including chemical means and physical means may be used for purification and isolation. Conventional purification means such as gel filtration, fractionation using a molecular weight fractionating membrane, solvent extraction, fractional distillation and various chromatographies using, for example, ion-exchange resins can be used in combination to purify and isolate the cyclopentenone derivative or an optical isomer thereof from the reaction product.

For example, a cyclopentenone derivative used in the present invention is produced by dissolving cyclopentenone or an optical isomer thereof, 4-dimethylaminopyridine and carboxylic acid in dichloromethane and adding N,N-dicyclohexylcarbodiimide thereto for reaction while cooling on ice. The cyclopentenone derivative of interest can be isolated by purifying the product on silica gel thin-layer cromatography.

Furthermore, diacetylcyclopentenone can be purified and isolated from a reaction product obtained by reacting cyclopentenone or an optical isomer thereof with acetic anhydride in anhydrous pyridine.

Optical isomers of the cyclopentenone derivatives used in the present invention can be separated by mechanical resolution of racemic mixture, preferential crystallization, resolution by crystallizing as a diastereomeric salt or an inclusion compound, kinetic resolution using an enzyme or a microorganism, chromatographic separation or the like.

Gas chromatography, liquid chromatography, thin-layer chromatography or the like using an appropriate chiral stationary phase can be used for chromatographic resolution.

A method in which a chiral stationary phase is used, a method in which a chiral eluent is used, separation as a diastereomer or the like can be used for optical resolution by liquid chromatography.

An amide-type stationary phase, a urea-type stationary phase, a ligand exchange-type stationary phase, a polysaccharide or polysaccharide derivative stationary phase, a protein stationary phase, a polymethacrylate ester stationary phase, a polymethacrylamide stationary phase or the like can be used as a chiral stationary phase.

A hexan-type eluent, an alcohol-type eluent, an aqueous (buffer) eluent or the like can be appropriately used as an eluent depending on the stationary phase used.

Salts of the cyclopentenone derivatives or optical isomers thereof used in the present invention include pharmaceutically acceptable salts. Known methods can be used for the conversion.

Representative examples of the cyclopentenone derivatives used in the present invention include diacetylcyclopentenone, dipropionylcyclopentenone, dibutyrylcyclopentenone, diisobutyrylcyclopentenone, divalerylcyclopentenone, dihexanoylcyclopentenone, dioctanoylcyclopentenone, didecanoylcyclopentenone, dimyristoylcyclopentenone, dimethoxyacetylcyclopentenone, dimethylfumarylcyclopentenone, dimethylmaleylcyclopentenone, di-2-hexenoylcyclopentenone, di-3-octenoylcyclopentenone and dibenzoylcyclopentenone.

The cyclopentenone derivative or an optical isomer thereof, or a salt thereof used in the present invention has an immunoregulatory activity, for example, an activity of inhibiting lymphocyte blastogenesis, an activity of inhibiting mixed lymphocyte reaction, an activity of activating natural killer cells, an activity of activating cancer cell-specific lymphocytes, an anti-inflammatory activity, for example, an activity of inhibiting carrageenan induced edema, an activity of inhibiting delayed hypersensitivity, an activity of inhibiting tumor necrosis factor production, an activity of inhibiting topoisomerase, an activity of inducing heat shock protein, an activity of inhibiting cell adhesion, an antifungal activity or the like. Based on these activities, the compound is useful as a pharmaceutical composition for treating or preventing a disease that requires immunoregulation for its treatment or prevention, a disease that requires suppression of inflammation for its treatment or prevention, a disease that requires inhibition of tumor necrosis factor production for its treatment or prevention, a disease that requires inhibition of topoisomerase, a disease that requires induction of heat shock protein for its treatment or prevention, a disease that requires growth inhibition of fungus for its treatment or prevention, a disease that requires inhibition of cell adhesion for its treatment or prevention or the like. Thus, an immunoregulatory composition, an anti-inflammatory composition, a composition for inhibiting tumor necrosis factor production, a composition for inhibiting topoisomerase, a composition for inducing heat shock protein, an antifungal composition and a composition for inhibiting cell adhesion can be produced using at least one compound selected from the group consisting of a cyclopentenone derivative or an optical isomer thereof, and a salt thereof as an active ingredient.

Tumor necrosis factor was discovered as a factor that induces hemorrhagic necrosis at tumor sites. Tumor necrosis factor is currently recognized as a cytokine that is involved widely in biological defense and immunological mechanism on the basis of inflammation. Failure in the regulatory mechanism of tumor necrosis factor production brings various troubles to the host. Overproduction or unregulated production of tumor necrosis factor is involved in a number of diseases. Such diseases include rheumatoid arthritis, rheumatic myelitis, osteoarthritis, gouty arthritis, sepsis, septic shock, endotoxin shock, Gram-negative bacterial sepsis, toxic shock syndrome, cerebral malaria, chronic pneumonia, graft versus host reaction, allograft rejection, pyrexia and myalgia due to an infectious disease such influenza, cachexia secondary to infection or malignant tumor, cachexia secondary to human acquired immunodeficiency syndrome (AIDS), AIDS, AIDS-related syndrome, keloid formation, ulcerative colitis, multiple sclerosis, and autoimmune diseases such as autoimmune diabetes and systemic lupus erythematosus [Molecular Medicine, 33: 1010–1020, 1182–1189 (1996)]. The composition for inhibiting tumor necrosis factor production of the present invention is useful for treating and preventing disease states mediated or worsened by tumor necrosis factor, for example, insulin-dependent diabetes mellitus caused by tumor necrosis factor [Nature, 389: 610–614 (1997)].

The present invention provides a method for regulating tumor necrosis factor production in which at least one compound selected from the group consisting of a cyclopentenone derivative or an optical isomer thereof and a salt thereof is used as an active ingredient. Furthermore, the present invention provides a food or a drink for ameliorating disease states of a disease mediated or worsened by tumor necrosis factor or a food or drink for preventing such disease containing at least one compound selected from the group consisting of a cyclopentenone derivative or an optical isomer thereof and a salt thereof.

The cyclopentenone derivative or an optical isomer thereof, or a salt thereof has immunoregulatory activities such as an activity of inhibiting lymphocyte blastogenesis and an activity of inhibiting mixed lymphocyte reaction. An immunoregulatory composition containing at least one compound selected from these compounds as an active ingredient is useful as a pharmaceutical composition for treating or preventing a disease due to abnormality in immune system or an immunological factor or a disease that requires immunopotentiation for its treatment or prevention.

Lymphocyte blastogenesis is a reaction in which mitogen binds to a receptor on the surface of a lymphocyte to activate the lymphocyte and promotes its division and proliferation. Mixed lymphocyte reaction is a reaction in which lymphocytes obtained from allogeneic animals are mixed and cultured, thereby inducing activation of lymphocytes due to incompatibility of major histocompatibility antigens to promote the division and proliferation of lymphocytes. The immunoregulatory composition inhibits these reactions and is particularly useful for treating and preventing autoimmune diseases caused by abnormal increase in lymphocytes, for example, chronic diseases such as chronic nephritis, chronic colitis, type I diabetes and rheumatoid arthritis and is also useful for suppression of graft rejection.

The cyclopentenone derivative or an optical isomer thereof, or a salt thereof has an activity of inhibiting carrageenan edema in foot. Thus, an anti-inflammatory composition containing at least one compound selected from these compounds as an active ingredient is useful as a pharmaceutical composition for treating or preventing a disease that requires suppression of inflammation for its treatment or prevention.

Carrageenan induced pedal edema model is a reaction in which inflammatory cells such as macrophages and neutrophils are induced by subcutaneously injecting an inflammatory agent carrageenan into a sole of foot, and inflammatory factors produced from these cells increase vascular permeability, resulting in edema. The activity of inhibiting edema of the anti-inflammatory composition is useful for treating or preventing a disease that requires suppression of increase in vascular permeability for its treatment or prevention, e.g., rheumatoid arthritis.

The cyclopentenone derivative or an optical isomer thereof, or a salt thereof has an activity of inhibiting delayed hypersensitivity. Thus, an anti-inflammatory composition containing at least one compound selected from these compounds as an active ingredient is useful as a pharmaceutical composition for treating or preventing a disease that requires inhibition of delayed hypersensitivity, which is caused by an infectious disease or the like, for its treatment or prevention.

Delayed hypersensitivity is an inflammatory reaction dependent on cellular immunity mediated by activated lymphocytes, monocytes, macrophages and the like. Cytokines produced from these cells infiltrating at inflammation sites increase vascular permeability, resulting in edema, granuloma, fibrosis and necrosis to cause severe disorders. Allergic dermatitis caused by delayed hypersensitivity accounts for majority of contact dermatitis. In addition, delayed hypersensitivity causes allergy in which a bacterium, a virus or a drug acts as an antigen. A mouse model using sheep erythrocyte as an antigen is generally used for testing delayed hypersensitivity. A compound that is effective in this model is considered to be useful for treating or preventing the above-mentioned allergic diseases.

The cyclopentenone derivative or an optical isomer thereof, or a salt thereof has an inhibitory activity on topoisomerase II. Topoisomerase II is transiently expressed only during division phase in normal cells. On the other hand, it is highly expressed throughout the cell cycle when cells cancerate. Thus, a composition for inhibiting topoisomerase containing at least one compound selected from these compounds as an active ingredient can be used as a carcinostatic. Furthermore, a method for inhibiting topoisomerase using at least one compound selected from these compounds as an active ingredient is useful for biochemical studies, screening of carcinostatics and the like.

The cyclopentenone derivative or an optical isomer thereof, or a salt thereof has an activity of inhibiting cell adhesion. Thus, there is provided a composition for inhibiting cell adhesion containing at least one compound selected from these compounds as an active ingredient. The composition for inhibiting cell adhesion of the present invention is useful as a pharmaceutical composition for treating or preventing a disease that requires inhibition of cell adhesion for its treatment or prevention.

For example, metastasis of cancer is established by release of cancer cells grown at primary lesion into blood vessels, migration to metastasis sites and infiltration into tissues. Among these, adhesion of the cancer cells to vascular endothelial cells is required for the migration of the cancer cells from the inside of blood vessels to the metastasis sites. ICAM-1, VCAM-1 and ELAM-1 on the vascular endothelial cells are known as adhesion molecules involved in metastasis of cancer. The corresponding ligands on the cancer cells have been identified as LFA-1, VLA-4 and sialyl Lewis X, respectively. These adhesion molecules are often expressed on leukemia cells and considered to be involved in extravascular infiltration of leukemia cells. Thus, the composition for inhibiting cell adhesion of the present invention is expected to inhibit the adhesion of cancer cells mediated by these adhesion molecules to inhibit metastasis of cancer.

Either of cyclopentenone and a compound produced from cyclopentenone and an SH group-containing compound as described in PCT/JP98/00815 also has an activity of inhibiting cell adhesion. Thus, there is provided a composition for inhibiting cell adhesion containing at least one compound selected from these compounds as an active ingredient.

The composition for inhibiting cell adhesion provided by the present invention can be used for a method for inhibiting cell adhesion. This method is useful for biochemical studies concerning cell adhesion and screening of cell adhesion inhibitors or agents having an activity of adhering cells.

The cyclopentenone derivative or an optical isomer thereof, or a salt thereof has an activity of activating natural killer (NK) cells. Thus, there is provided a composition for activating NK cells containing at least one compound selected from these compounds as an active ingredient. The composition for activating NK cells of the present invention is useful as a pharmaceutical composition for treating or preventing a disease that requires activation of NK cells for its treatment or prevention.

NK cells recognize cells infected with bacteria or viruses and cancer cells, and eliminate these cells by cell membrane attack. Activation of NK cells enhances the immunological protection mechanism in a living body. Thus, the composition for activating NK cells of the present invention is useful for treating or preventing a bacterial or viral disease and cancer.

Either of cyclopentenone and a compound produced from cyclopentenone and an SH group-containing compound as described in PCT/JP98/00815 also has an activity of activating NK cells. Thus, there is provided a composition for activating NK cells containing at least one compound selected from these compounds as an active ingredient.

The composition for activating NK cells provided by the present invention can be used for a method for activating NK cells. This method is useful for biochemical studies concerning immunological protection mechanism and screening of immunoprotective agents.

The cyclopentenone derivative or an optical isomer thereof, or a salt thereof has an antifungal activity. Thus, an antifungal composition can be produced by using at least one compound selected from these compounds as an active ingredient and formulating it with a known pharmaceutical carrier.

A number of agents have been conventionally used for treating fungal infection, including amphotericin B, flucytosine, miconazole and fluconazole. However, they have problems concerning the efficacy and toxicity, or strains resistant thereto. In particular, less toxic agents effective for systemic infection, which tends to increase recently, are few. The antifungal component of the present invention is useful as a new type of an antifungal agent since it is less toxic.

The cyclopentenone derivative or an optical isomer thereof, or a salt thereof has an activity of inducing heat shock protein. Thus, a composition for inducing heat shock protein can be produced by using at least one compound selected from these compounds as an active ingredient. The composition can be administered through a suitable route for a disease that requires induction of heat shock protein for its treatment or prevention.

The cyclopentenone derivative or an optical isomer thereof, or a salt thereof has an activity of inducing heat shock proteins such as 70-kDa heat shock protein (HSP70). They have antiviral activities against RNA viruses and DNA viruses such as hepatitis virus, AIDS virus, influenza virus, vesicular stomatitis virus and herpesvirus. Heat shock proteins are involved in tumor immunity. Thus, these compounds are also effective for tumor immunity. In addition, these compounds also have activities of biological defense such as an anti-inflammatory activity. Thus, viral diseases such as a cold due to influenza virus can be prevented or treated by administering the compound of the present invention or an optical isomer thereof, or a salt thereof.

Heat shock protein is a generic name of proteins of which the synthesis is induced when a cell or an individual is subjected to rapid change in temperature to one higher by 5 to 10° C. than normal temperature. Heat shock proteins are distributed in wide variety of organisms including prokaryotes and higher eukaryotes. HSP90, HSP70, ubiquitin, HP26 and the like are known as eukaryotic heat shock proteins. Among these, HSP70 is one of molecular chaperones which bind to proteins that have not completely folded or incompletely folded proteins and assist their three-dimensional structure formation. Amino acid sequences of heat-shock proteins are well conserved in the course of evolution. HSP70 is homologous to *Escherichia coli* DnaK protein. About ten HSP70 genes are present in human. Some of them are constitutively expressed whereas others are induced by various stimuli. Synthesis of heat shock protein is induced by various chemical substances and cell damages such as oxidative stress in addition to heat shock.

C. Amici et al. [Journal of Virology, 68:6890–6899 (1994)] reports that cultivation of animal cells infected with Sendai virus in the presence of prostaglandin $A_1$ having $\alpha,\beta$-unsaturated carbonyl induces the synthesis of SP70 and HSP90 and that synthesis of viral proteins is suppressed while the synthesis of HSP70 is induced. A. Rossi et al. [The Journal of Biological Chemistry, 271:32192–32196 (1996)] reports that 2-cyclopenten-1-one, like prostaglandin $A_1$, induces the synthesis of HSP70 and suppresses the synthesis of proteins from vesicular stomatitis virus.

For example, the ability of diisobutyrylcyclopentenone, a cyclopentenone derivative, to induce HSP70 is observed at a concentration of 1.25 $\mu$M. It is maximized at a concentration of 2.5 $\mu$M. This inducing ability is very high as compared with that of 2-cyclopenten-1-one, which is required to be used at a concentration of several hundred $\mu$M for inducing HSP70.

The cyclopentenone derivative or an optical isomer thereof, or a salt thereof has antiviral activities against DNA viruses, RNA viruses, retroviruses and viroids base on the high activity of inducing heat shock protein. The viruses and viroids are exemplified by the above-mentioned ones.

Generally, the immunoregulatory composition can be produced by using a compound selected from the group consisting of a cyclopentenone derivative or an optical isomer thereof, and a salt thereof as its active ingredient, and mixing it with a pharmaceutically acceptable liquid or solid carrier and, optionally, solvent, dispersing agent, emulsifier, buffering agent, stabilizer, excipient, binder, disintegrant, lubricant and the like to formulate it. The formulation may be in a form of a solid preparation such as tablet, granule, powder, epipastic and capsule, or a liquid preparation such as normal solution, suspension and emulsion. In addition, the composition may be formulated into a dried preparation, which can be reconstituted as a liquid preparation by adding an appropriate carrier before use.

The pharmaceutical carrier can be selected according to the above-mentioned particular administration route and dosage form. For an oral preparation, starch, lactose, sucrose, mannit, carboxymethylcellulose, cornstarch, inorganic salts and the like are utilized, for example. Binder, disintegrant, surfactant, lubricant, fluidity-promoting agent, tasting agent, coloring agent, flavoring agent and the like can also be included in oral preparations.

A parenteral preparation can be prepared according to conventional methods by dissolving or suspending the active ingredient of the present invention, i.e., a compound selected from the group consisting of a cyclopentenone derivative or an optical isomer thereof, and a salt thereof, in a diluent. The diluents include injectable distilled water, physiological saline, aqueous glucose solution, injectable vegetable oil, sesame oil, peanut oil, soybean oil, corn oil, propylene glycol and polyethylene glycol. Optionally, sterilizer, stabilizer, osmotic regulator, smoothing agent and the like may be added to the solution or suspension.

The immunoregulatory composition of the present invention is administered through a suitable route for the dosage form of the composition. The administration route is not limited to a specific one. The composition can be administered internally or externally (or topically) or by injection. The injectable preparation can be administrated intravenously, intramuscularly, subcutaneously, intradermally and the like, for example. External preparations include a suppository.

A dosage of the immunoregulatory composition is appropriately determined and varies depending on the particular dosage form, administration route and purpose as well as age, weight and conditions of a patient to be treated. In general, a daily dosage for an adult person is 0.1 $\mu$g to 200 mg/kg in terms of the amount of a compound selected from the group consisting of cyclopentenone or an optical isomer thereof, and a salt thereof contained in the formulation. Of course, the dosage can vary depending on various factors.

Therefore, in some cases, a less dosage than the above may be sufficient but, in other cases, a dosage more than the above may be required. The pharmaceutical composition of the present invention can be administrated orally as it is, or it can be taken daily by adding to selected foods and drinks.

The composition for inhibiting tumor necrosis factor production, the anti-inflammatory composition, the composition for inhibiting topoisomerase, the composition for inhibiting cell adhesion, the composition for inducing heat shock protein and the antifungal composition of the present invention can be formulated according to the same manner as that described above with respect to the immunoregulatory composition. They can be administered through a suitable route for the disease of interest. Of course, the dosage of the composition can vary depending on various factors. Therefore, in some cases, a less dosage than the above may be sufficient but, in other cases, a dosage more than the above may be required. The pharmaceutical composition of the present invention can be administrated orally as it is, or it can be taken daily by adding to selected foods and drinks.

The cyclopentenone derivative or an optical isomer thereof, or a salt thereof used in the present invention can be efficiently produced from cyclopentenone and any one of carboxylic acids or reactive derivatives thereof.

There are provided diisobutyrylcyclopentenone (a product of reaction between cyclopentenone and isobutyric anhydride), dimethoxyacetylcyclopentenone (a product of reaction between cyclopentenone and methoxyacetic acid), dimethylfumarylcyclopentenone and dimethylmaleylcyclopentenone (products of reaction between cyclopentenone and methylmaleic acid) according to the above-mentioned production method.

These compounds have a carcinostatic activity, an activity of inhibiting topoisomerase and the like. Pharmaceutical compositions such as a carcinostatic composition can be produced by using these compounds or optical isomers thereof, or salts thereof as their active ingredients.

The process for producing a food or a drink containing the cyclopentenone derivative or an optical isomer thereof, or a salt thereof obtained according to the present invention as its active ingredient is not limited to a specific one. Any processes including cooking, processing and other generally employed processes for producing a food or a drink can be used as long as the resultant food or drink contains an effective amount of a compound having a physiological activity selected from the group consisting of a cyclopentenone derivative or an optical isomer thereof, and a salt thereof. A functional food or drink such as an immunoregulatory food or drink can be thus produced.

No toxicity is observed when a physiologically effective amount of the cyclopentenone derivative or an optical isomer thereof, or a salt thereof obtained according to the present invention is administered. For example, no death was observed when either one of dipropionylcyclopentenone, dihexanoylcyclopentenone, di-2-hexenoylcyclopentenone, diisobutyrylcyclopentenone, dibenzoylcyclopentenone or optical isomers thereof, or salts thereof was orally administered to a mouse at a single dosage of 100 mg/kg.

As described above, the cyclopentenone derivative or an optical isomer thereof, or a salt thereof can be conveniently produced and are very useful in a wide variety of fields including medicine and foods based on their various physiological functions.

The following examples further illustrate the present invention in detail but are not to be construed to limit the scope thereof. Percent (%) in Examples means percent by weight.

EXAMPLE 1

(1) 10 g of D-glucuronic acid (Sigma, G 5269) was dissolved in 1 liter of water. The solution was heated at 121° C. for 4 hours and then concentrated to a volume of about 10 ml under reduced pressure. 40 ml of an upper layer of a mixture of butyl acetate:acetic acid:water=3:2:2 was added thereto and mixed. A supernatant obtained by centrifuging the mixture was concentrated under reduced pressure to a volume of about 10 ml.

The extract was applied to silica gel BW-300SP for column chromatography (2×28 cm, Fuji Sylysia) Separation was carried out using an upper layer of butyl acetate:acetic acid:water=3:2:2 as an eluent, at a pressure of 0.2 kg/cm$_2$ using a compressor and at a flow rate of 5 ml/min. Each fraction contained 10 ml of the fractionated eluate. A portion of each fraction was analyzed on thin-layer chromatography. As a result, 61st to 80th fractions contained cyclopentenone with high purity. These fractions were collected and concentrated under reduced pressure. The concentrate was extracted with 40 ml of chloroform. The extract was concentrated under reduced pressure to obtain 100 mg of cyclopentenone.

The preparation was separated on normal phase HPLC using Palpack Type S column and detected on the basis of ultraviolet absorbance at 215 nm. This procedure confirmed that the preparation had a purity of 98%. 113.9 mg of cyclopentenone obtained according to the method as described above was dissolved in 2.85 ml of ethanol. 3.85 ml of hexane/ethanol (94/6) was further added to the solution in ethanol to prepare 17 mg/ml cyclopentenone solution. This solution was filtrated through a 0.5-μm filter to obtain a sample solution for optical resolution HPLC.

The sample solution was subjected to optical resolution HPLC under the conditions as described below. Fractions containing a (−) isomer and a (+) isomer of cyclopentenone were separately collected from the former peak and the latter peak, respectively. The fractions were evaporated to dryness under reduced pressure to obtain 43.2 mg of the (−) isomer and 43.0 mg of and the (+) isomer of cyclopentenone.

Conditions for optical resolution HPLC

Column: Chiralpack AS (Dicel Chemical Industries) 2.0 cm×25.0 cm;

Column temperature: 40° C.;

Mobile phase: hexan/ethanol (94/6);

Flow rate: 14.0 ml/min.;

Detection: UV 210 nm;

Amount of sample injected: 150 μl (2.55 mg).

Since both of the resulting (−) isomer and (+) isomer of cyclopentenone contained an enantiomer at a concentration of about 1%, they were optically resolved again under the above-mentioned conditions. As a result, 19.7 mg of the (−) isomer of cyclopentenone free of an enantiomer was obtained from 30.0 mg of the (−) isomer from the former peak. 27.7 mg of the (+) isomer of cyclopentenone free of an enantiomer was obtained from 37.4 mg of the (+) isomer from the latter peak. The elution time in the optical resolution HPLC for the (−) isomer of cyclopentenone was 33 min. and that for the (+) isomer was 40 min.

(2) 1 ml of anhydrous pyridine (Nacalai Tesque, 295-26) and 0.1 ml of acetic anhydride (Nacalai Tesque, 002-26) were added to 29.6 mg of cyclopentenone obtained as described in Example 1-(1). The mixture was stirred at is room temperature for 3 hours. The reaction mixture was extracted with chloroform to obtain 36 mg of diacetylcyclopentenone.

Mass spectrometric analysis of the resulting diacetylcyclopentenone was carried out using DX302 mass spectrometer (Nippon Denshi). Additionally, diacetylcyclopentenone was dissolved in $CDCl_3$ and subjected to structural analysis by NMR using a nuclear magnetic resonance apparatus JNM-A500 (Nippon Denshi). The results are shown below. The chemical shift values in $^1$H-NMR are expressed assuming the chemical shift value of chloroform as 7.24 ppm.

MS m/z 199 $(M+H)^+$; $^1$H-NMR; δ 2.12 (3H, S, —$OCOCH_3$), 2.16 (3H, S, —$OCOCH_3$), 5.16 (1H, d, J=3.0 Hz, H-5), 5.89 (1H, m, H-4), 6.40 (1H, d-d, J=1.5, 6.5 Hz, H-2), 7.43 (1H, d-d, J=2.5, 6.5 Hz, H-3).

(3) 15.9 mg of the (−) isomer of cyclopentenone obtained as described in Example 1-(1) was used to carry out the reaction as described in Example 1-(2) to obtain 15.1 mg of a diacetyl (−) isomer of cyclopentenone. Similar results with those in Example 1-(2) were obtained when the isomer was subjected to structural analysis by mass spectrometry and nuclear magnetic resonance as described in Example 1-(2).

(4) 16.7 mg of the (+) isomer of cyclopentenone obtained as described in Example 1-(1) was used to carry out the reaction as described in Example 1-(2) to obtain 18.8 mg of a diacetyl (+) isomer of cyclopentenone. Similar results with those in Example 1-(2) were obtained when the isomer was subjected to structural analysis by mass spectrometry and nuclear magnetic resonance as described in Example 1-(2).

(5) 44.3 mg of benzoic acid (Nacalai Tesque, 041-20), 7.5 mg of dimethylaminopyridine (DMAP; Tokyo Kasei Kogyo, D1450), 51.0 mg of N,N'-dicyclohexylcarbodiimide (DCC: Peptide Institute, 1001) and 5 ml of chloroform were added to 13.8 mg of cyclopentenone. The mixture was stirred on ice for 4 hours. A filtrate obtained by the filtration of the reaction mixture was applied to silica gel column (75 ml) and eluted with chloroform to obtain fractions containing dibenzoylcyclopentenone. The solvent in the fractions was removed under reduced pressure, the residue was dissolved in ethanol, and the solution was separated on silica gel thin-layer chromatography using a 99:1 mixture of chloroform and methanol as a developing solvent. Silica gel at Rf=0.45–0.55 was scraped from the thin layer and extracted with chloroform to obtain 3.2 mg of dibenzoylcyclopentenone.

Structural analysis by mass spectrometry and nuclear magnetic resonance of the thus obtained dibenzoylcyclopentenone was carried out as described in Example 1-(2). The results are shown below.

MS m/z 323 $(M+H)^+$; $^1$H-NMR; δ 5.56 (1H, d, J=3.0 Hz, H-5), 6.30 (1H, m, H-4), 6.54 (1H, d-d, J=1.5, 6.5 Hz, H-2), 7.44 (4H, m, H of aromatic ring), 7.58 (2H, m, H of aromatic ring), 7.64 (1H, d-d, J=2.0, 6.5 Hz, H-3), 8.06 (4H, m, H of aromatic ring).

(6) 22.1 mg of the (−) isomer of cyclopentenone, 71.9 mg of benzoic acid, 12.1 mg of DMAP and 80.3 mg of DCC were used to carry out the reaction as described in Example 1-(5) to obtain 19.2 mg of a dibenzoyl (−) isomer of cyclopentenone. Similar results with those in Example 1-(5) were obtained when the isomer was subjected to structural analysis by mass spectrometry and nuclear magnetic resonance as described in Example 1-(5).

(7) 20.4 mg of the (+) isomer of cyclopentenone, 65.6 mg of benzoic acid, 11.0 mg of DMAP and 74.3 mg of DCC were used to carry out the reaction as described in Example 1-(5) to obtain 21.4 mg of a dibenzoyl (+) isomer of cyclopentenone. Similar results with those in Example 1-(5) were obtained when the isomer was subjected to structural analysis by mass spectrometry and nuclear magnetic resonance as described in Example 1-(5).

(8) 30 mg of cyclopentenone, 10 mg of DMAP and 153 mg of hexanoic acid (Nacalai Tesque, 070-26) were dissolved in 5.9 ml of dichloromethane. 108 mg of DCC was added thereto while cooling on ice. After reacting for 1 hour, the reaction mixture was separated and purified on silica gel thin-layer chromatography using chloroform as a developing solvent. Silica gel at Rf=0.3–0.4 was scraped from the thin layer and extracted with chloroform to obtain 11 mg of dihexanoylcyclopentenone.

The thus obtained dihexanoylcyclopentenone was dissolved in $CDCl_3$ for confirmation by nuclear magnetic resonance (NMR) using a nuclear magnetic resonance apparatus JNM-EX270 FT NMR system (Nippon Denshi). The chemical shift values in $^1$H-NMR are expressed assuming the chemical shift value of tetramethylsilane as 0 ppm.

The results are shown below.

$^1$H-NMR; δ 7.44 (1H, dd, $J_{2-3}$=6.27 Hz, $J_{3-4}$=1.98 Hz, H-3), 6.42 (1H, dd, $J_{2-3}$=6.27 Hz, $J_{3-4}$=1.32 Hz, H-2), 5.91 (1H, m, H-4), 5.16 (1H, d, $J_{4-5}$=2.97 Hz, H-5), 2.42 (2H, t, J=7.26 Hz), 2.38 (2H, t, J=7.76 Hz), 1.65 (4H, m), 1.26 (8H, m), 0.88 (6H, t).

(9) 30 mg of cyclopentenone, 10 mg of DMAP and 301 mg of myristic acid (Tokyo Kasei Kogyo, M0476) were dissolved in 5.9 ml of dichloromethane. 108 mg of DCC was added thereto while cooling on ice. After reacting for 1 hour, the reaction mixture was separated on silica gel thin-layer chromatography using chloroform as a developing solvent. Silica gel at Rf=0.45–0.55 was scraped from the thin layer and extracted with chloroform to obtain 53 mg of dimyristoylcyclopentenone.

Structural analysis by nuclear magnetic resonance of the thus obtained dimyristoylcyclopentenone was carried out as described in Example 1-(8). The results are shown below.

$^1$H-NMR; δ 7.45 (1H, dd, $J_{2-3}$=5.94 Hz, $J_{3-4}$=2.31 Hz, H-3), 6.42 (1H, dd, $J_{2-3}$=5.31 Hz, $J_{3-4}$=1.32 Hz, H-2), 5.92 (1H, m, H-4), 5.16 (1H, d, $J_{4-5}$=2.64 Hz, H-5), 2.42 (2H, t, J=7.26 Hz), 2.38 (2H, t, J=7.91 Hz), 1.63 (4H, m), 1.26 (32H, m), 0.88 (6H, t).

(10) 30 mg of cyclopentenone, 10 mg of DMAP and 190 mg of octanoic acid (Nacalai Tesque, 071-11) were dissolved in 5.9 ml of dichloromethane. 108 mg of DCC was added thereto while cooling on ice. After reacting for 1 hour, the reaction mixture was separated on silica gel thin-layer chromatography using chloroform as a developing solvent. Silica gel at Rf=0.25–0.35 was scraped from the thin layer and extracted with chloroform to obtain 27 mg of dioctanoylcyclopentenone.

Structural analysis by nuclear magnetic resonance of the thus obtained dioctanoylcyclopentenone was carried out as described in Example 1-(8). The results are shown below.

$^1$H-NMR; δ 7.44 (1H, dd, $J_{2-3}$=6.1 Hz, $J_{3-4}$=2.16 Hz, H-3), 6.41 (1H, dd, $J_{2-3}$=6.1 Hz, $J_{3-4}$=1.48 Hz, H-2), 5.92 (1H, m, H-4), 5.16 (1H, d, $J_{4-5}$=2.97 Hz, H-5), 2.42 (2H, t, J=7.59 Hz), 2.38 (2H, t, J=7.91 Hz), 1.65 (4H, m), 1.29 (16H, m), 0.88 (6H, t).

(11) 30 mg of cyclopentenone, 10 mg of DMAP and 190 mg of 3-octenoic acid (Tokyo Kasei Kogyo, 00070) were dissolved in 5.9 ml of dichloromethane. 108 mg of DCC was added thereto while cooling on ice. After reacting for 1 hour, the reaction mixture was separated on silica gel thin-layer chromatography using chloroform as a developing solvent. Silica gel at Rf=0.25–0.35 was scraped from the thin layer and extracted with chloroform to obtain 25 mg of di-3-octenoylcyclopentenone.

Structural analysis by nuclear magnetic resonance of the thus obtained di-3-octenoylcyclopentenone was carried out as described in Example 1-(8). The results are shown below.

¹H-NMR; δ 7.44 (1H, dd, $J_{2-3}$=6.27 Hz, $J_{3-4}$=2.32 Hz, H-3), 6.42 (1H, dd, $J_{2-3}$=6.27 Hz, $J_{3-4}$=1.49 Hz, H-2), 5.91 (1H, m, H-4), 5.55 (4H, m), 5.16 (1H, d, $J_{4-5}$=2.97 Hz, H-5), 3.12 (4H, dd, J=12.85 Hz, J=6.59 Hz), 2.04 (4H, m), 1.33 (8H, m), 0.89 (6H, t).

(12) 30 mg of cyclopentenone, 10 mg of DMAP and 115 mg of n-butyric acid (Tokyo Kasei Kogyo, B0754) were dissolved in 5.9 ml of dichloromethane. 108 mg of DCC was added thereto while cooling on ice. After reacting for 1 hour, the reaction mixture was separated on silica gel thin-layer chromatography using chloroform as a developing solvent. Silica gel at Rf=0.20–0.30 was scraped from the thin layer and extracted with chloroform to obtain 16 mg of dibutyryl-cyclopentenone.

Structural analysis by nuclear magnetic resonance of the thus obtained dibutyrylcyclopentenone was carried out as described in Example 1-(8). The results are shown below.

¹H-NMR; δ 7.45 (1H, dd, $J_{2-3}$=6.27 Hz, $J_{3-4}$=2.13 Hz, H-3), 6.42 (1H, dd, $J_{2-3}$=6.27 Hz, $J_{3-4}$=1.65 Hz, H-2), 5.91 (1H, m, H-4), 5.16 (1H, d, $J_{4-5}$=2.64 Hz, H-5).

(13) 30 mg of cyclopentenone, 10 mg of DMAP and 226 mg of n-decanoic acid (Tokyo Kasei Kogyo, D0017) were dissolved in 5.9 ml of dichloromethane. 108 mg of DCC was added thereto while cooling on ice. After reacting for 1 hour, the reaction mixture was separated on silica gel thin-layer chromatography using chloroform as a developing solvent. Silica gel at Rf=0.35–0.45 was scraped from the thin layer and extracted with chloroform to obtain 35 mg of dide-canoylcyclopentenone.

Structural analysis by nuclear magnetic resonance of the thus obtained didecanoylcyclopentenone was carried out as described in Example 1-(8). The results are shown below.

¹H-NMR; δ 7.44 (1H, dd, $J_{2-3}$=6.27 Hz, $J_{3-4}$=1.97 Hz, H-3), 6.42 (1H, dd, $J_{2-3}$=6.27 Hz, $J_{3-4}$=1.3 Hz, H-2), 5.91 (1H, m, H-4), 5.15 (1H, d, $J_{4-5}$=2.97 Hz, H-5), 2.42 (2H, t, J=7.24 Hz), 2.38 (2H, t, J=7.91 Hz), 1.65 (4H, m), 1.26 (24H, m), 0.88 (6H, t).

(14) 30 mg of cyclopentenone, 16 mg of DMAP, 66 mg of triethylamine (Tokyo Kasei Kogyo, T0424) and 122 mg of n-valeric anhydride (Tokyo Kasei Kogyo, V0006) were dissolved in 5.9 ml of dichloromethane. The mixture was reacted on ice for 1 hour. The reaction mixture was developed on silica gel thin-layer chromatography using chloroform:methanol 200:1 as a developing solvent. Silica gel at Rf=0.7–0.8 was scraped from the thin layer and extracted with chloroform to obtain 39 mg of divalerylcyclopentenone.

Structural analysis by nuclear magnetic resonance of the thus obtained divalerylcyclopentenone was carried out as described in Example 1-(8). The results are shown below.

¹H-NMR; δ 7.45 (1H, dd, J2-3=6.11 Hz, J3-4=1.66 Hz, H-3), 6.42 (1H, dd, J2-3=6.11 Hz, J3-4=1.66 Hz, H-2), 5.91 (1H, m, H-4), 5.16 (1H, d, J4-5=2.97 Hz, H-5), 2.43 (2H, dd, J=7.59, 7.59 Hz), 2.39 (2H, dd, J=7.59, 7.59 Hz), 1.65 (4H, m), 1.38 (4H, m), 0.93 (6H, dd, J=7.26, 7.26 Hz).

(15) 30 mg of cyclopentenone, 16 mg of DMAP, 66 mg of triethylamine and 86 mg of propionic anhydride (Tokyo Kasei Kogyo, P0513) were dissolved in 5.9 ml of dichloromethane. The mixture was reacted on ice for 1 hour. The reaction mixture was developed on silica gel thin-layer chromatography using chloroform:methanol=200:1 as a developing solvent. Silica gel at Rf=0.5–0.6 was scraped from the thin layer and extracted with chloroform to obtain 31 mg of dipropionylcyclopentenone.

Structural analysis by nuclear magnetic resonance of the thus obtained dipropionylcyclopentenone was carried out as described in Example 1-(8). The results are shown below.

¹H-NMR; δ 7.45 (1H, dd, J2-3=6.27 Hz, J3-4=2.15 Hz, H-3), 6.42 (1H, dd, J2-3=6.27 Hz, J3-4=1.49 Hz, H-2), 5.91 (1H, m, H-4), 5.16 (1H, d, J4-5=2.97 Hz, H-5), 2.46 (2H, dd, J=15.01, 7.59 Hz), 2.42 (2H, dd, J=15.01, 7.59 Hz), 1.18 (6H, dd, J=7.59, 7.59 Hz).

(16) 2 g of cyclopentenone, 733 mg of DMAP, 4.1 ml of trans-2-hexenoic acid (Tokyo Kasei Kogyo, H0383) and 5.57 g of DCC were dissolved in 200 ml of dichloromethane. The mixture was reacted at room temperature for 2 hours. The reaction mixture was subjected to silica gel column chromatography using hexane:ethyl acetate=8:1 as a solvent to obtain a fraction that results in a single spot on silica gel thin-layer chromatography. The fraction was concentrated under reduced pressure to obtain about 900 mg of oil of di-2-hexenoylcyclopentenone.

Structural analysis by nuclear magnetic resonance of the thus obtained di-2-hexenoylcyclopentenone was carried out as described in Example 1-(8). The results are shown below.

¹H-NMR; δ 0.92 (6H, m, 11-H+11'-H), 1.48 (4H, m, 10-H+10'-H), 2.18 (4H, m, 9-H, 9'-H), 5.22 (1H, d, J=3.0 Hz, 5-H), 5.85 (2H, m, 7-H+7'-H), 5.98 (1H, m, 4-H), 6.41 (1H, dd, J=1.0, 6.0 Hz, 2-H), 7.04 (2H, m, 8-H+8'-H), 7.47 (1H, dd, J=2.0, 6.0 Hz, 3-H).

The positions of carbons in the 2-hexenoyl group attached at 5-position of cyclopentenone were defined as 6-position to 11-position starting from the carbonyl group. The positions of carbons in the 2-hexenoyl group attached at 4-position of cyclopentenone were defined as 6'-position to 11'-position starting from the carbonyl group.

(17) 1.2 g of cyclopentenone was dissolved in 200 ml of dichloromethane. 1.7 ml of isobutyric anhydride (Nacalai Tesque), 427 mg of DMAP and 1.46 ml of triethylamine (Nacalai Tesque) were added thereto. The mixture was reacted at room temperature for 1 hour and concentrated under reduced pressure. The residue was dissolved in ethyl acetate and washed with 10% citric acid and saturated aqueous sodium hydrogencarbonate solution. The solution was concentrated under reduced pressure. The concentrate was separated on silica gel column chromatography using hexane:ethyl acetate=8:1 as a developing solvent to obtain a fraction that results in a spot at Rf=0.2 on silica gel thin-layer chromatography using hexane:ethyl acetate=6:1 as a developing solvent. The solvent in the fraction was removed by evaporating under reduced pressure to obtain 470 mg of oil containing diisobutyrylcyclopentenone with high purity.

Structural analysis by nuclear magnetic resonance of the thus obtained diisobutyrylcyclopentenone dissolved in heavy chloroform was carried out as described in Example 1-(2). The results are shown below.

¹H-NMR; δ 1.18 (12H, m, 7-H, 8-H, 10-H, 11-H), 2.61 (2H, m, 6-H, 9-H), 5.10 (1H, d, J=3.0 Hz, 5-H), 5.88 (1H, m, 4-H), 6.39 (1H, dd, J=1.5, 6.0 Hz, 2-H), 7.41 (1H, dd, J=2.5, 6.0 Hz, 3-H).

The results are expressed assuming the chemical shift value of the residual proton of heavy chloroform as 7.24 ppm.

The ¹H-NMR spectrum of diisobutyrylcyclopentenone is illustrated in FIG. 1. In FIG. 1, the horizontal axis represents the chemical shift value (ppm) and the vertical axis represents the signal intensity.

The numbers for signal identification in ¹H-NMR are as indicated in formula [III] below.

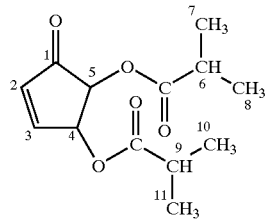

[III]

(18) 1.5 g of cyclopentenone was dissolved in 200 ml of dichloromethane. 2.7 g of methoxyacetic acid (Nacalai Tesque), 794 mg of DMAP and 5.36 g of dicyclohexylcarbodiimide (DCC; Nacalai Tesque) were added thereto. The mixture was reacted at room temperature for 2 hours and concentrated under reduced pressure. The residue was dissolved in ethyl acetate and washed with 10% citric acid and saturated aqueous sodium hydrogencarbonate solution. The solution was concentrated under reduced pressure. The concentrate was separated on silica gel column chromatography using hexane:ethyl acetate=2:3 as a developing solvent to obtain a fraction that results in a spot at Rf=0.34 on silica gel thin-layer chromatography using hexane:ethyl acetate=1:1 as a developing solvent. The solvent in the fraction was removed by evaporating under reduced pressure to obtain 300 mg of oil containing dimethoxyacetylcyclopentenone with high purity.

Structural analysis by nuclear magnetic resonance of the thus obtained dimethoxyacetylcyclopentenone dissolved in heavy chloroform was carried out as described in Example 1-(2). The results are shown below.

$^1$H-NMR; δ 3.45 (6H, s, 7-H, 9-H), 4.13 (4H, m, 6-H, 8-H), 5.30 (1H, d, J=3.0 Hz, 5-H), 5.99 (1H, m, 4-H), 6.44 (1H, dd, J=1.5, 6.5 Hz, 2-H), 7.46 (1H, dd, J=2.0, 6.5 Hz, 3-H).

The results are expressed assuming the chemical shift value of the residual proton of heavy chloroform as 7.24 ppm.

Figure 2:
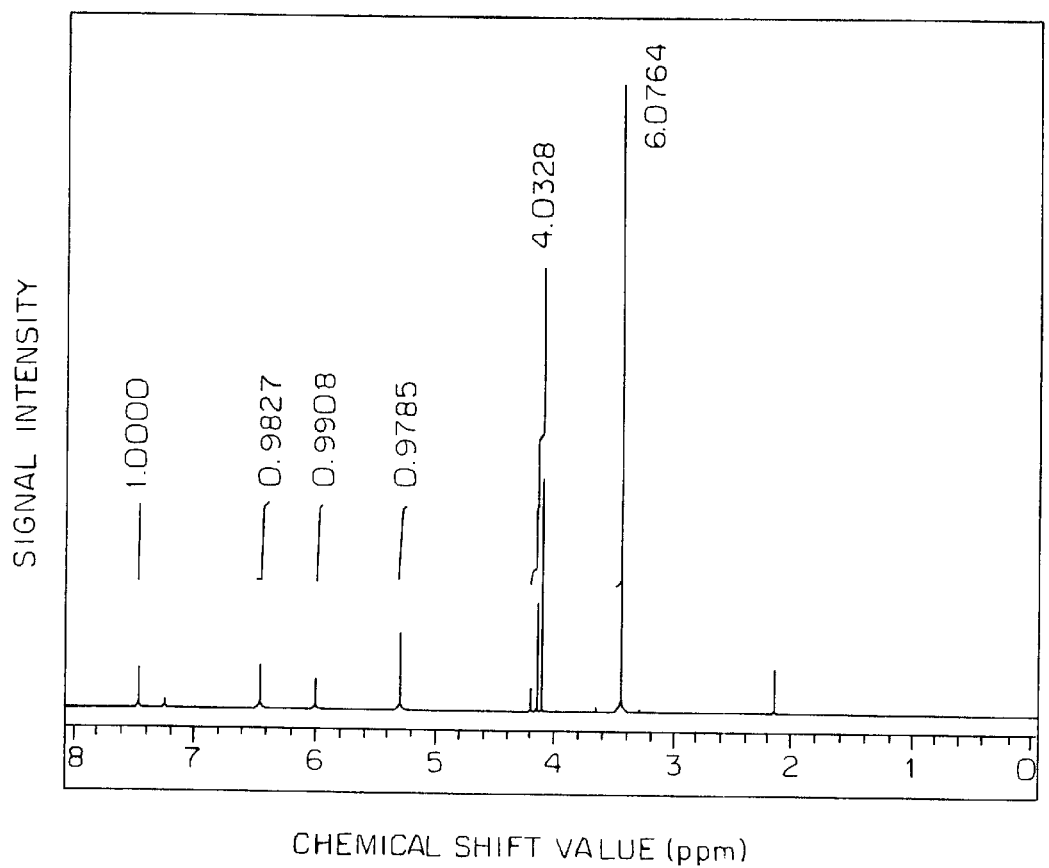
FIG. 2 illustrates the $^1$H-NMR spectrum of dimethoxyacetylcyclopentenone.

The $^1$H-NMR spectrum of dimethoxyacetylcyclopentenone is illustrated in FIG. 2. In FIG. 2, the horizontal axis represents the chemical shift value (ppm) and the vertical axis represents the signal intensity.

The numbers for signal identification in $^1$H-NMR are as indicated in formula [IV] below.

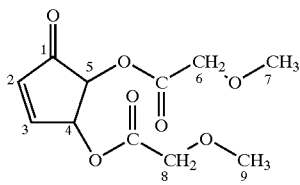

[IV]

(19) 1.1 g of cyclopentenone was dissolved in 200 ml of dichloromethane. 3.4 g of methylmaleic acid, 610 mg of DMAP and 4.12 g of dicyclohexylcarbodiimide were added thereto. The mixture was reacted at room temperature for 2 hours and concentrated under reduced pressure. The residue was dissolved in ethyl acetate and washed with 10% citric acid and saturated aqueous sodium hydrogencarbonate solution. The solution was concentrated under reduced pressure. The concentrate was separated on silica gel column chromatography using hexane:ethyl acetate=3:2 as a developing solvent to obtain a fraction that results in a spot at Rf=0.6 and a fraction that results in a spot at Rf=0.45 on silica gel thin-layer chromatography using hexane:ethyl acetate=1:1 as a developing solvent.

The solvent in the fractions was removed by evaporating under reduced pressure to obtain 300 mg of solid containing dimethylfumarylcyclopentenone with high purity from the Rf=0.6 fraction and 300 mg of oil containing dimethylmaleylcyclopentenone with high purity from the Rf=0.45 fraction.

Structural analysis by nuclear magnetic resonance of the products dissolved in heavy chloroform was carried out as described in Example 1-(2). The results are shown below.

$^1$H-NMR;
Dimethylfumarylcyclopentenone

δ 3.80 (6H, s, 10-H, 15-H), 5.31 (1H, d, J=3.0 Hz, 5-H), 6.03 (1H, m, 4-H), 6.48 (1H, dd, J=1.0, 6.0 Hz, 2-H), 6.90 (4H, m, 7-H, 8-H, 12-H, 13-H), 7.50 (1H, dd, J=2.0, 6.0 Hz, 3-H).

Dimethylmaleylcyclopentenone

δ 3.76 (6H, s, 10-H, 15-H), 5.31 (1H, d, J=3.0 Hz, 5-H), 6.07 (1H, m, 4-H), 6.31 (4H, m, 7-H, 8-H, 12-H, 13-H), 6.44 (1H, dd, J=1.5, 6.0 Hz, 2-H), 7.58 (1H, dd, J=2.0, 6.0 Hz, 3-H).

The results are expressed assuming the chemical shift value of the residual proton of heavy chloroform as 7.24 ppm.

Figure 3:
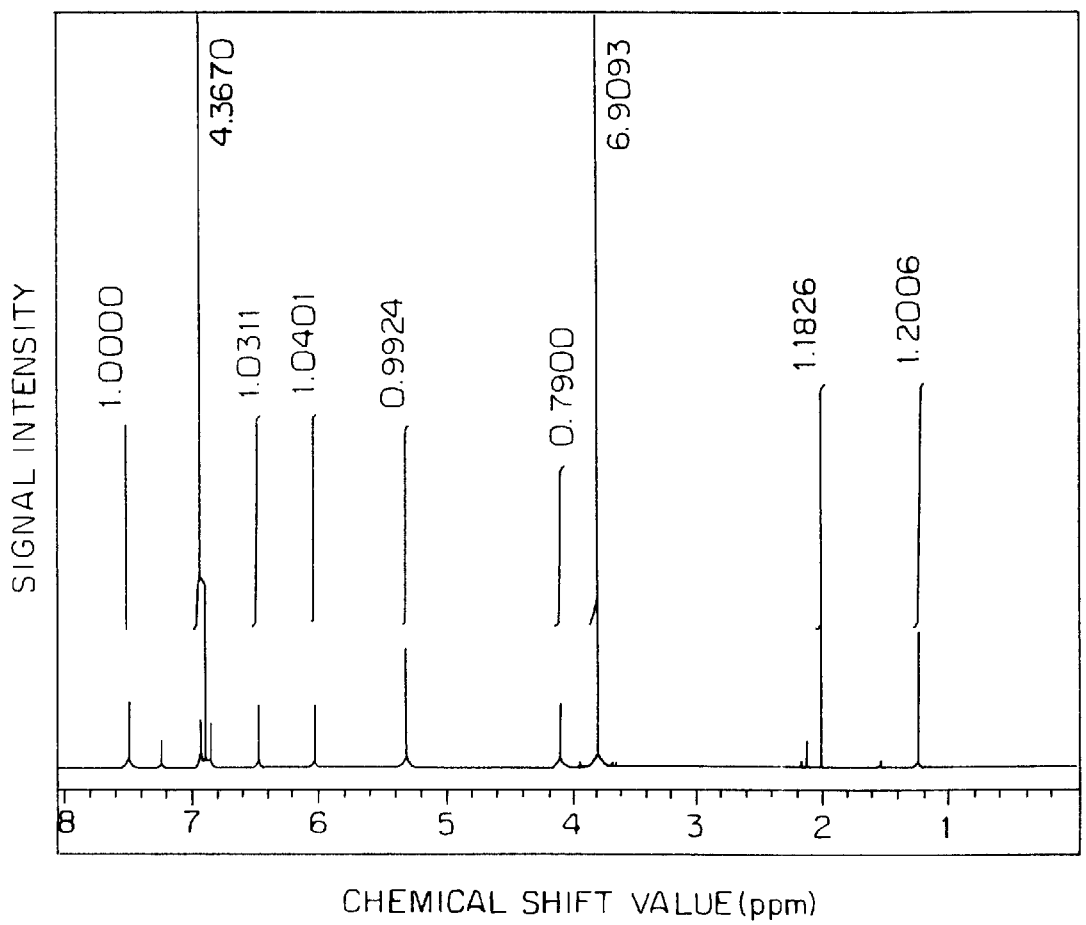
FIG. 3 illustrates the $^1$H-NMR spectrum of dimethylfumarylcyclopentenone.
Figure 4:
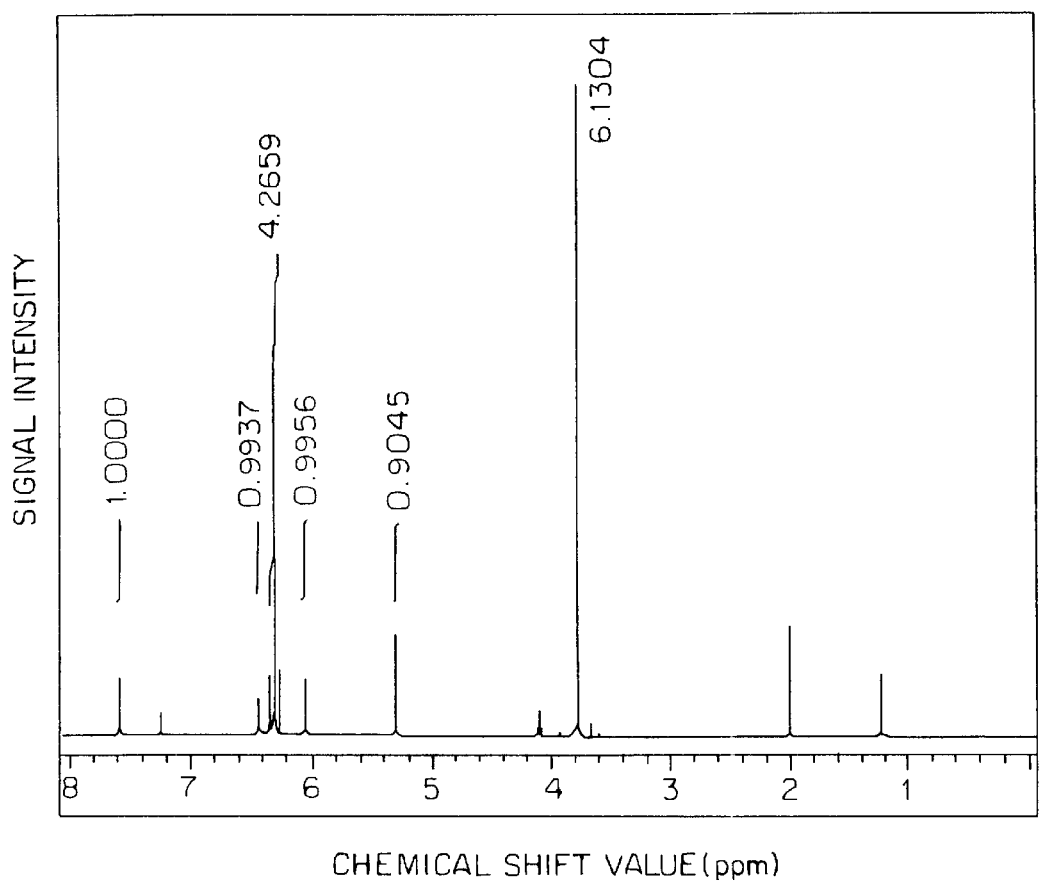
FIG. 4 illustrates the $^1$H-NMR spectrum of dimethylmaleylcyclopentenone.

The $^1$H-NMR spectrum of dimethylfumarylcyclopentenone is illustrated in FIG. 3. The $^1$H-NMR spectrum of dimethylmaleylcyclopentenone is illustrated in FIG. 4. In FIGS. 3 and 4, the horizontal axes represent the chemical shift value (ppm) and the vertical axes represent the signal intensity.

The numbers for signal identification in $^1$H-NMR for dimethylfumarylcyclopentenone are as indicated in formula [V] below.

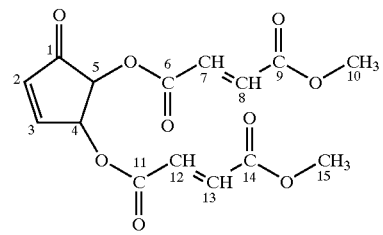

[V]

The numbers for signal identification in $^1$H-NMR for dimethylmaleylcyclopentenone are as indicated in formula [IV] below.

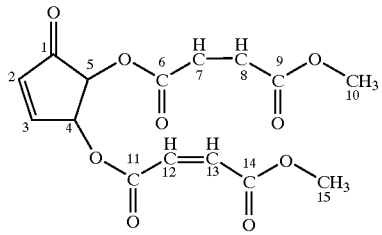

[VI]

(20) 100 μl of 1M aqueous cyclopentenone solution and 500 μl of 200 mM aqueous glutathione (reduced; Nacalai Tesque, 170-10) solution (pH 3.0) were mixed together. The mixture was reacted at 60° C. for 5 hours. The reaction mixture was filtrated through a 0.5-μm Cosmonice filter and separated on HPLC under the following conditions.

Column: TSKgel ODS-80Ts (5 μm) 20 mm×25 cm;

Mobile Phase A: 0.1% aqueous TFA solution;

B: aqueous solution containing 0.1% TFA/50% acetonitrile;

Flow rate: 7.5 ml/min.;

Gradient: Mobile Phase A (10 min.)→Mobile Phase A to A:B=1:1 (55 min.)→A:B=1:1 to Mobile Phase B (15 min.);

Detection: absorbance at 220 nm.

200 μl of the reaction mixture was subjected to HPLC. Peaks at retention time of 35.7 min. and 36.1 min. were collected and evaporated to dryness under reduced pressure to obtain 5.5 mg of dry solid.

The structure of the dry solid was analyzed. Measurements were carried out using JNM-A500 (Nippon Denshi) for nuclear magnetic resonance (NMR) spectrum, DX302 mass spectrometer (Nippon Denshi) for mass spectrum (MS), UV-2500 spectrophotometer (Shimadzu) for ultraviolet (UV) absorption spectrum and FTIR-8000PC infrared spectrometer (Shimadzu) for infrared absorption (IR) spectrum, respectively. The results are shown below.

$^1$H-NMR; δ 2.09 (2H, m, 5'-H), 2.28 (1H, dd, J=13.0, 20.0 Hz, 5-H), 2.44 (2H, m, 4'-H), 2.78 (1H, dd, J=8.5, 14.0, 1'-H), 2.85 or 2.89 (1H, dd, J=3.0, 6.0 Hz, 5-H), 2.92 or 2.95 (1H, dd, J=1.0, 5.5 Hz, 1'-H), 3.86 (2H, S, 9'-H), 3.95 (2H, m, 4-H, 6'-H), 4.46 (1H, m, 2'-H), 6.47 or 6.49 (1H, d, J=3.0 Hz, 3-H)

The sample was dissolved in 0.1 N DCl solution in heavy water. The results are expressed assuming the chemical shift value of HOD as 4.65 ppm.

$^{13}$C-NMR; δ 26.3 (5'-C), 31.7 (4'-C), 31.9 or 32.1 (1'-C), 39.3 (4-C), 41.9 (9'-C), 42.2 or 42.3 (5-C), 53.3 (6'-C), 54.1 (2'-C), 133.5 (3-C), 154.4 (2-C), around 173 (3'-C, 7'-C, 8'-C, 10'-C), 205.8 (1-C).

The sample was dissolved in 0.1 N DCl solution in heavy water. The results are expressed assuming the chemical shift value of dioxane as 67.4 ppm.

The numbers for peak identification in $^1$H-NMR and $^{13}$C-NMR are as indicated in formula [VII] below.

[VII]

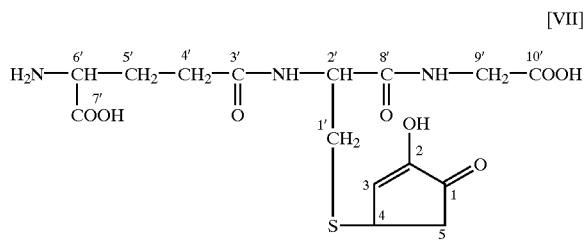

FAB-MS; m/z 404 (M+H)$^+$, 426 (M+Na)$^+$.

Glycerol was used for matrix.

UV $\lambda_{max}$ 251 nm (water); IR $\nu^{KBr}_{max}$ cm$^{-1}$ 2949, 1710, 1660, 1539, 1404, 1203. Measurement was carried out according to diffuse reflectance method.

These results revealed that the dry solid was 2-hydroxy-4-glutathion-S-yl-2-cyclopenten-1-one (hereinafter simply referred to as GM).

EXAMPLE 2

HL-60 (ATCC CCL-240) cells were cultured at 37° C. in RPMI 1640 medium (Bio Whittaker) containing 10% fetal calf serum (FCS; JRH) which had been treated at 56° C. for 30 minutes and suspended in RPMI 1640 medium at a concentration of 2.5×10$^5$ cells/5 ml.

10 μl each of solutions of diisobutyrylcyclopentenone, dimethoxyacetylcyclopentenone, dimethylfumarylcyclopentenone or dimethylmaleylcyclopentenone in 70% ethanol in water diluted to varying concentrations was added to 5 ml of the suspension. The mixtures were incubated at 37° C. for 24 hours in the presence of 5% Co$_2$. 10 μl of aqueous actinomycin D (Sigma) solution (0.5 mg/ml), which is known as a reagent that induces apoptosis, was used in place of the sample and the mixture was incubated under the same conditions for confirmation.

The cultured cells were examined under an optical microscope. Condensation of nuclei, shrinking of cells and formation of apoptotic bodies were observed for the cells cultured with the addition of the samples and actinomycin D. No such phenomenon was observed for the control cells cultured with the addition of 10 μl of 70% aqueous ethanol solution.

Furthermore, a portion of the cells cultured as described above was stained with 0.4% Trypan Blue and examined under an optical microscope. The number of viable cells which were not stained and the number of dead cells which were stained blue were counted. The concentration of each of the samples that results in a viability of 50% (Viability$_{50}$ μM) was determined. The results are shown in Table 1.

TABLE 1

| Sample | Viability$_{50}$ (μM) |
| --- | --- |
| Diisobutyrylcyclopentenone | 8.8 |
| Dimethoxyacetylcyclopentenone | 14 |
| Dimethylfumarylcyclopentenone | 2.9 |
| Dimethylmaleylcyclopentenone | 3.4 |

As described above, each compound exhibited an antiproliferation activity against tumor cells and an apoptosis-inducing activity. In addition, optical isomers of the respective compounds and salts thereof exhibited similar activities.

EXAMPLE 3

(1) 2 μl of topoisomerase II (TopoGEN; 2 units/μl), 2 μl of 10-fold concentrated buffer [0.5 M Tris-HCl (pH 8.0), 1.2 M KCl, 0.1 M MgCl$_2$, 2.5 mM adenosine triphosphate, 5 mM dithiothreitol], 2 μl of 0.1% bovine serum albumin (Takara Shuzo), 11 μl of distilled water and 2 μl of distilled water (control) or 2 μl of one of aqueous solutions of dipropionylcyclopentenone, diisobutyrylcyclopentenone, dibenzoylcyclopentenone, dihexanoylcyclopentenone, di-2-hexenoylcyclopentenone, dimethoxyacetylcyclopentenone, dimethylfumarylcyclopentenone or dimethylmaleylcyclopentenone at varying concentrations were mixed together. 1 μl of 0.25 μg/μl pBR322 DNA (Takara Shuzo) was added thereto. The resulting mixture was reacted at 37° C. After reacting for 30 minutes, 2 μl of an aqueous solution containing 1% sodium dodecyl sulfate, 50% glycerol and 0.02% Bromophenol Blue was added thereto to stop the reaction.

20 μl of the reaction mixture was applied to 1% agarose gel prepared using agarose L03 (Takara Shuzo) and TAE buffer [40 mM Tris, 5 mM sodium acetate, 1 mm ethylenediaminetetraacetic acid disodium salt (EDTA); adjusted to pH 7.8 using acetic acid] and electrophoresed in TAE buffer. After electrophoresis, the gel was soaked in a 1 μg/ml aqueous ethidium bromide solution. The gel was exposed to ultraviolet rays to visualize the electophoretic pattern of DNA. The form of DNA is completely changed from superhelical type to relaxed type for a control to which water is added, whereas the change from superhelical type to relaxed type is partially or completely inhibited if topoisomerase II activity is inhibited.

As a result, the form of DNA was completely changed from superhelical type to relaxed type for a control to which water was added. On the other hand, the change in the form of the DNA from superhelical type to relaxed type was partially or completely inhibited by dipropionylcyclopentenone at a concentration of 0.1 µM or more, diisobutyrylcyclopentenone at a concentration of 1 µM or more, dibenzoylcyclopentenone at a concentration of 1 µM or more, dihexanoylcyclopentenone at a concentration of 10 µM or more, di-2-hexenoylcyclopentenone at a concentration of 10 µM or more, dimethoxyacetylcyclopentenone at a concentration of 50 µM or more, dimethylfumarylcyclopentenone at a concentration of 10 µM or more or dimethylmaleylcyclopentenone at a concentration of 5 µM or more, confirming the activity of inhibiting topoisomerase II of each of the cyclopentenone derivatives.

(2) The activity of inhibiting topoisomerase I of each of the cyclopentenone derivatives was determined as described in Example 3-(1) except that topoisomerase I (TopoGEN; 0.01 unit/µl) was used in place of topoisomerase II and a solution containing 100 mM Tris-HCl (pH 7.9), 10 mM EDTA, 1 mM spermidine and 50% glycerol was used as 10-fold concentrated buffer.

As a result, the form of DNA was completely changed from superhelical type to relaxed type for a control to which water was added. On the other hand, the change in the form of the DNA from superhelical type to relaxed type was partially or completely inhibited by dipropionylcyclopentenone at a concentration of 1000 µM or more, diisobutyrylcyclopentenone at a concentration of 500 µM or more, dibenzoylcyclopentenone at a concentration of 50 µM or more, dihexanoylcyclopentenone at a concentration of 1000 µM or more, di-2-hexenoylcyclopentenone at a concentration of 500 µM or more, dimethoxyacetylcyclopentenone at a concentration of 1000 µM or more, dimethylfumarylcyclopentenone at a concentration of 1000 µM or more or dimethylmaleylcyclopentenone at a concentration of 1000 µM or more, confirming the activity of inhibiting topoisomerase I of each of the cyclopentenone derivatives.

As described above, each of the above-mentioned cyclopentenone derivatives as well as other cyclopentenone derivatives as described in Example 1 exhibited an inhibitory activity on topoisomerase II. Topoisomerase II is transiently expressed only during division phase in normal cells, whereas it is highly expressed throughout the cell cycle when cells cancerate. The inhibitory activity on topoisomerase II was stronger than that on topoisomerase I of which the expression level and activity are increased upon canceration.

In addition, optical isomers of the respective compounds and salts thereof exhibited similar inhibitory activities specific for topoisomerase II.

EXAMPLE 4

(1) 5 ml of RPMI 1640 medium containing 10% fetal calf serum and HL-60 (ATCC CCL-240) cells at a concentration of $2 \times 10^5$ cells/ml was placed in each well of a 6-well plate. The plate was incubated at 37° C. for 24 hours in the presence of 5% $CO_2$. Dipropionylcyclopentenone, diisobutyrylcyclopentenone or di-2-hexenoylcyclopentenone at a final concentration of 0, 0.63, 1.3, 2.5, 5, 10 or 20 µM was then added thereto. The incubation was continued for additional 6 hours.

After incubation, the cell number was counted. The cells were harvested by centrifugation, washed with PBS to prepare cells treated with one of the samples. Cells that were cultured in the same manner after heated at 45° C. for 10 minutes were also prepared.

These treated cells were used for SDS-PAGE according to the method as described in Molecular Cloning [Cold Spring Harbor Laboratory Press (1989)]. The treated cells were suspended in SDS-PAGE Sample buffer at a concentration of $2.5 \times 10^6$ cells/ml. The cell suspensions were treated at 100° C. for 10 minutes. 5 µl each of the cell suspensions was applied to two SDS-PAGE gels (5% stacking gel, 10% separation gel) and electrophoresed. One of the gels was subjected to Coomassie staining. The other gel was blotted onto a polyvinylidene difluoride transfer membrane (Immobilon™, Millipore, Cat. #IPVH000-10). The membrane was blocked at 4° C. overnight using Block Ace (Dainippon Pharmaceutical, Cat. #UK-B25).

The blocked membrane was reacted with a monoclonal antibody HSP72/73(Ab-1) (Oncogene Research Products, Cat. #HSP01), which specifically reacts with heat-inducible 70-kDa heat shock protein. The membrane was washed with TBS containing 0.05% Tween 20 followed by TBS. The membrane was then reacted with a peroxidase-conjugated secondary antibody HRP-Rabbit Anti-Mouse IgG (H+L) (Zymed Laboratories, Inc., Cat. #61-6520), and then washed as described above. The membrane reacted with the primary and secondary antibodies was reacted with a chemiluminol reagent Renaissance™ (Dupont NEN, Cat. #NEL-100). The membrane was then exposed to an X-ray film to confirm the induction of 70-kDa heat shock protein.

As a result, the induction of 70-kDa heat shock protein was observed. The degree of the induction is shown in Table 2. In Table 2, + represents the induction level. Increased number of + means increased induction. − means that no induction was observed. ± means that a slight induction was observed.

TABLE 2

| Cyclopentenone derivative | Concentration (µM) | | | | | |
|---|---|---|---|---|---|---|
| | 0.63 | 1.3 | 2.5 | 5 | 10 | 20 |
| Dipropionyl-cyclopentenone | − | ± | + | +++ | ++ | ++ |
| Diisobutyryl-cyclopentenone | ± | + | +++ | +++ | + | + |
| Di-2-hexenoyl-cyclopentenone | ± | + | ++ | +++ | ± | − |

The result for untreated control was −, and the result for the cells cultured after heating at 45° C. for 10 minutes was ++. As described above, each of the above-mentioned compounds exhibited an activity of inducing heat shock protein at a low concentration. In addition, optical isomers of the respective compounds and salts thereof exhibited similar activities. Furthermore, other cyclopentenone derivatives or optical isomers thereof, or salts thereof exhibited similar activities.

EXAMPLE 5

Dipropionylcyclopentenone, diisobutyrylcyclopentenone and di-2-hexenoylcyclopentenone were used to examine their antifungal activities against *Candida albicans* TIMM0136.

*Candida albicans* cells were cultured overnight in YNBG medium containing 0.67% Yeast Nitrogen Base (Difco) and 1.0% glucose (seed culture). The culture was then diluted with fresh Yeast Nitrogen Base medium to a concentration of $1 \times 10^6$ cells/ml. 100 µl of the dilution was dispensed into each well of a 96-well microtiter plate.

10 μl each of solutions of dipropionylcyclopentenone, diisobutyrylcyclopentenone or di-2-hexenoylcyclopentenone in 70% ethanol at a concentration of 100 μg/ml or 500 μg/ml, or 10 μl of 70% ethanol solution was added to the well. The plate was incubated without shaking at 30° C. for 48 hours (main culture).

Dipropionylcyclopentenone, diisobutyrylcyclopentenone or di-2-hexenoylcyclopentenone suppressed the growth of *Candida albicans* at a concentration of 500 μg/ml. The minimum growth inhibitory concentration of each compound was 500 μg/ml. Thus, these compounds are useful as active ingredients for antifungal compositions. In addition, optical isomers of the cyclopentenone derivatives and salts thereof exhibited similar activities.

EXAMPLE 6

Human vascular endothelial cells (sold by Sanko Junyaku) suspended in RPMI-1640 medium (Gibco) containing 10% FCS (HyClone) at a concentration of $1 \times 10^5$ cells/ml. 100 μl/well of the suspension was seeded into a 96-well microtiter plate.

100 U/ml of human recombinant TNF-α (Promega) was added to monolayer of vascular endothelial cells after incubation at 37° C. for 2 days in a 5% $CO_2$ incubator. The plate was incubated 37° C. for 6 hours in a 5% $CO_2$ incubator to prepare vascular endothelial cells stimulated with TNF-α.

On the other hand, cyclopentenone, GM or dipropionylcyclopentenone at a varying concentration was added to HL-60 cells suspended in RPMI-1640 medium containing 10% FCS at a concentration of $1 \times 10^6$ cells/ml. The cells were cultured at 37° C. for 3 hours in a 5% $CO_2$ incubator. After cultivation, 5 μM of 5(-and-6)-carboxyfluorescein diacetate, succinimide ester (Molecular Probe) as a fluorescent agent was added thereto and reacted at 37° C. for 10 minutes. The cells were washed twice with RPMI-1640 medium and suspended in RPMI-1640 medium containing 10% FCS to prepare a suspension of fluorescence-labeled HL-60 cells at a concentration of $1 \times 10^6$ cells/ml.

100 μl/well of the fluorescence-labeled HL-60 cells were overlaid onto the vascular endothelial cells stimulated with TNF-α. Cyclopentenone, GM or dipropionylcyclopentenone at a varying concentration was added thereto. The plate was incubated at 37° C. for 20 minutes in a 5% $CO_2$ incubator for adhesion reaction between vascular endothelial cells and HL-60 cells.

After the adhesion reaction, the plate was washed to remove non-adhesive cells. 1% Triton X (Nacalai Tesque) was added thereto to destroy adhesive cells. The fluorescence intensity was measured using filters for 485/22 nm (excitation) and 530/25 nm (emission).

The adhesion rate which represents the ratio of cells adhered to vascular endothelial cells was determined defining the fluorescence intensity for $1 \times 10_5$ fluorescence-labeled cells as 100%.

The results are shown in Table 3. The rate of adhesion of vascular endothelial cells to HL-60 was increased when they were stimulated with TNF-α. This increase in adhesion rate was suppressed by cyclopentenone, GM or dipropionylcyclopentenone at a concentration ranging from $10^{-7}$ to $10^{-4}$ M in a dose-dependent manner. Thus, each of cyclopentenone, GM and dipropionylcyclopentenone exhibited an activity of inhibiting adhesion between cancer cells and vascular endothelial cells, which is required for the inhibition of metastasis of cancer. In addition, optical isomers of the respective compounds and salts thereof exhibited similar activities.

Furthermore, other cyclopentenone derivatives or optical isomers thereof, or salts thereof exhibited similar activities.

TABLE 3

| Test substance | Concentration (μM) | Adhesion rate (%) |
| --- | --- | --- |
| Control | | |
| Unstimulated | | 3.6 |
| Stimulated with TNF-α | | 50.9 |
| Cyclopentenone | | |
| | 0.1 | 51.7 |
| | 1 | 46.0 |
| | 10 | 22.2 |
| | 100 | 17.9 |
| GM | | |
| | 0.1 | 53.9 |
| | 1 | 48.3 |
| | 10 | 23.9 |
| | 100 | 16.3 |
| Dipropionylcyclopentenone | | |
| | 0.1 | 49.2 |
| | 1 | 35.1 |
| | 10 | 15.3 |
| | 100 | 15.5 |

EXAMPLE 7 ddY mice (female, 7 weeks old) were purchased from Japan SLC and pre-bred 1 week before using in experiments.

$1 \times 10^6$ Ehrlich ascites carcinoma cells were intraperitoneally inoculated to each mouse. 10 mg/kg of cyclopentene, 30 mg/kg of GM or 10 mg/kg of dipropionylcyclopentene was intraperitoneally administered to the mouse on the day after the inoculation. Saline was administered to a control mouse.

A spleen was taken out from the mouse 10 days after the inoculation with cancer cells, finely minced and suspended in RPMI-1640 medium (Gibco) containing 10% FCS (HyClone) to obtain a single cell suspension. Adhesive cells in the cell suspension adhered to a plastic Petri dish were removed and non-adhesive cells were used as spleen lymphocytes.

The spleen lymphocytes were suspended in RPMI-1640 medium containing 10% FCS at a concentration of $2 \times 10^6$/ml. 100 μl/well of the suspension was seeded into a microtiter plate.

Stimulated cells were prepared as follows. Mitomycin C (Kyowa Hakko Kogyo) was added to a concentration of 50 μg/ml to Ehrlich ascites carcinoma cells suspended in RPMI-1640 medium at a concentration of $2 \times 10^6$ cells/ml. The cells were treated at 37° C. for 30 minutes, washed twice and then suspended in RPMI-1640 medium containing 10% FCS to prepare stimulated cells at a concentration of $2 \times 10^6$ cells/ml. 100 μl of the thus prepared stimulated cells was overlaid onto each well of the plate into which 100 μl/well of the spleen lymphocytes had been added. The plate was incubated at 37° C. for 5 days in a 5% $CO_2$ incubator. 37 kBq of $^3$H-thymidine (Daiichi Pure Chemicals) was added to the well to pulse-label the cells on the day before the completion of the cultivation. After cultivation, the cells were harvested on a glass filter to measure the radioactivity.

The results are shown in Table 4. The growth of spleen lymphocytes obtained from mice administered with cyclopentenone, GM or dipropionylcyclopentenone were significantly enhanced by stimulation with cancer cells, suggesting that lymphocyte specifically reactive with cancer cells were induced. In addition, optical isomers of the respective compounds and salts thereof exhibited similar activities.

Furthermore, other cyclopentenone derivatives or optical isomers thereof, or salts thereof exhibited similar activities.

TABLE 4

| Test substance | Dose (mg/kg) | Stimulation with cancer cell | $^3$H-thymidine uptake (CPM) |
| --- | --- | --- | --- |
| Control | | − | 10492 |
| | | + | 8806 |
| Cyclopentenone | 10 | − | 9680 |
| | | + | 25756 |
| GM | 30 | − | 8700 |
| | | + | 36291 |
| Dipropionyl-cyclopentenone | 10 | − | 9250 |
| | | + | 20748 |

EXAMPLE 8 ddY mice (female, 7 weeks old) were purchased from Japan SLC and pre-bred for 1 week before using in experiments.

$1 \times 10^6$ Ehrlich ascites carcinoma cells were intraperitoneally inoculated to each mouse. 10 mg/kg of cyclopentenone, 30 mg/kg of GM or 10 mg/kg of dipropionylcyclopentenone was intraperitoneally administered to the mouse on the day after the inoculation. Saline was administered to a control mouse.

A spleen was taken out from the mouse 10 days after the inoculation with cancer cells, finely minced and suspended in RPMI-1640 medium containing 10% FCS (HyClone) to obtain a single cell suspension. Adhesive cells adhered to a plastic Petri dish were removed from the cell suspension and non-adhesive cells were used as NK cells.

The NK cells were suspended in RPMI-1640 medium containing 10% FCS at a concentration of $6 \times 10^6$/ml. 100 $\mu$l/well of the suspension was seeded into a microtiter plate.

Target cells were prepared as follows. 3700 kBq of $^{51}$Cr (Amersham) was added to $1 \times 10^6$ YAC-1 cells (Dainippon Pharmaceutical). The cells were cultured at 37° C. for 1 hour for labeling. The labeled cells were washed twice and then suspended in RPMI-1640 medium containing 10% FCS at a concentration of $2 \times 10^5$ cells/ml. 100 $\mu$l of the thus prepared target cells were overlaid onto each well of the plate into which NK cells had been added. The plate was incubated at 37° C. for 5 hours in a 5% $CO_2$ incubator. After incubation, the plate was centrifuged at 1500 rpm for 5 minutes. 100 $\mu$l of the supernatant was collected in a gamma counter tube. The radioactivity (experimental value) was measured using an auto gamma counter.

100 $\mu$l of the culture medium was added to the reaction system in place of the NK cells and the radioactivity was measured in order to measure the radioactivity spontaneously released from the target cells (control value).

Furthermore, the radioactivity released into the supernatant when 1% Triton (Nacalai Tesque) was added to the reaction system to lyse the $_{51}$Cr-labeled YAC-1 cells was measured in order to measure the total radioactivity contained in the reaction system (total radioactivity value).

The cytotoxicity (%) specifically mediated by the NK cells can be determined according to the following equation.

Cytotoxicity (%)=[(experimental value−control value)/ (total radioactivity value−control value)]×100

The results are shown in Table 5. Activation of NK cells was observed in mice administered with cyclopentenone, GM or dipropionylcyclopentenone. The administration of these compounds increased the immunological protection mechanism in a living body and cytotoxic activity against cancer cells. In addition, optical isomers of the respective compounds and salts thereof exhibited similar activities.

Furthermore, other cyclopentenone derivatives or optical isomers thereof, or salts thereof exhibited similar activities.

TABLE 5

| Test substance | Dose (mg/kg) | Cytotoxicity (%) |
| --- | --- | --- |
| Control | | 3.5 |
| Cyclopentenone | 10 | 15.5 |
| GM | 30 | 19.0 |
| Dipropionyl-cyclopentenone | 10 | 13.5 |

EXAMPLE 9

Lewis rats (male, 9 weeks old, weighing about 250 g) were purchased from Seac Yoshitomi.

Rats were fasted from 18 hours before the start of the experiments. Dipropionylcyclopentenone, dihexanoylcyclopentenone, di-2-hexenoylcyclopentenone, diisobutyrylcyclopentenone or dibenzoylcyclopentenone dissolved in olive oil (Nacalai Tesque) was orally administered to 4 rats per group at 1 or 10 mg/10 ml/kg.

100 $\mu$l of 1% λ-carrageenan (Wako Pure Chemical Industries) suspension in saline (Otsuka Pharmaceutical) was injected into the sole of right paw of a rat 0.5 hour after the administration of test substance to induce pedal edema. The volume of the right foot of the rat was measured using an instrument for measuring pedal volume (Ugo Basile) 3 hours after the injection with carrageenan. The measurements were expressed as the rate of increase calculated based on the volume of the right foot of each rat measured before the administration with carrageenan.

Figure 5:
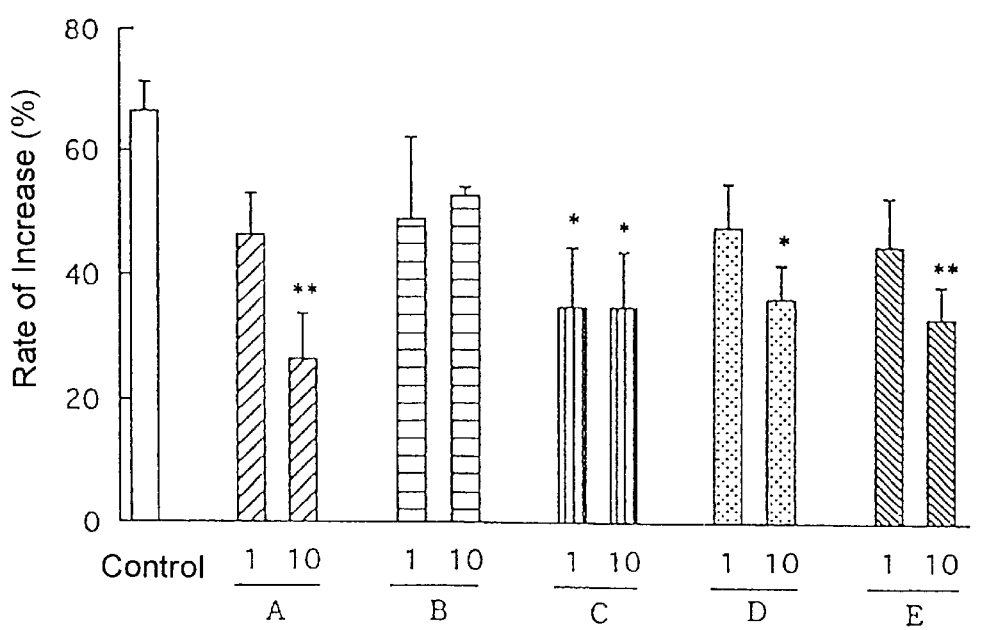
FIG. 5 illustrates the relationship between the amount of cyclopentenone derivative administered and the rate of increase in edema in foot.

The results are shown in FIG. 5. FIG. 5 illustrate the relationship between the amount of cyclopentenone derivative administered and the rate of increase in edema in foot. The horizontal axis represents the dose (mg/ml) and the vertical axis represents the rate of increase (%).

Tendency to suppress the edema in the foot was observed when dipropionylcyclopentenone was administered at 1 mg/kg. Administration at 10 mg/kg resulted in significant suppression. Administration of dihexanoylcyclopentenone or di-2-hexenoylcyclopentenone at 1 or 10 mg/kg resulted in significant suppression. Tendency of suppression was observed when diisobutyrylcyclopentenone or dibenzoylcyclopentenone was administered at 1 mg/kg. Administration at 10 mg/kg resulted in significant suppression. In addition, optical isomers of the cyclopentenone derivatives and salts thereof exhibited similar activities.

Furthermore, other cyclopentenone derivatives or optical isomers thereof, or salts thereof exhibited similar activities.

In FIG. 5, marks * and ** represent significant differences of $p<0.05$ and $p<0.01$ as compared with the control group, respectively.

EXAMPLE 10

C57BL/6 mice (male, 7 weeks old, weighing about 25 g) were purchased from Japan SLC and pre-bred for 1 week before using in experiments.

Sheep erythrocytes (Shimizu Laboratory Supplies) as raising antigens were washed three times with saline (Otsuka Pharmaceutical) and suspended in saline at a concentration of 1×10$^9$ cells/ml. 200 μl of the suspension was intraperitoneally injected into the mouse for sensitization with the antigen. 40 μl of similarly prepared antigen was injected to the sole of right paw 5 days after the sensitization for antigenic induction to induce pedal edema.

Dipropionylcyclopentenone dissolved in saline at a varying concentration was intraperitoneally or orally administered to 5 mice per group once a day for 3 days from the day of sensitization with the antigen. The volume of the right foot of the mouse was measured using an instrument for measuring pedal volume (Ugo Basile) 2 days after the antigenic induction and used as an index of DTH. The measurements were expressed as the rate of increase calculated according to the following equation based on the volume of the right foot of each mouse measured before the antigenic induction.

Figure 6:
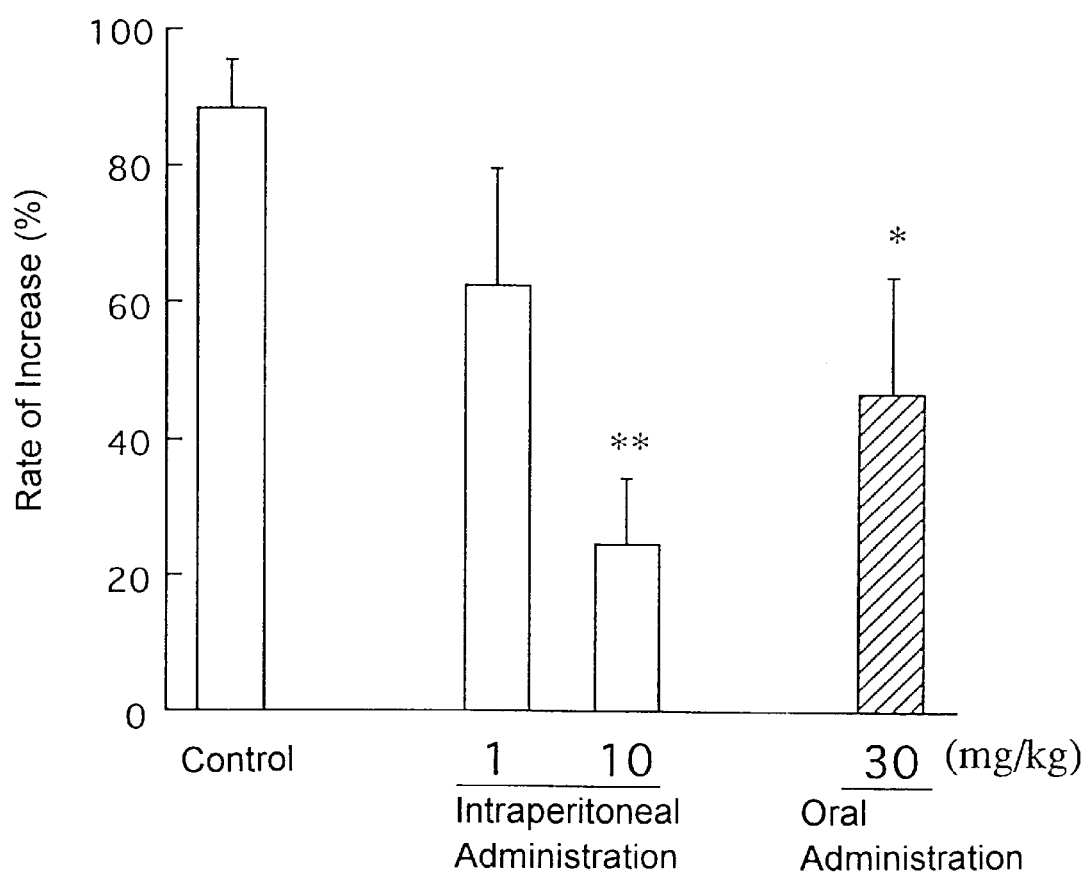
FIG. 6 illustrates the relationship between the amount of cyclopentenone derivative administered and the rate of increase in delayed hypersensitivity.

Rate of increase=(volume of right foot after antigenic induction−volume of right foot before antigenic induction)/volume of right foot before antigenic induction The results are shown in FIG. 6. In FIG. 6, the vertical axis represents the rate of increase in the volume of foot increased by the antigenic induction. Tendency to suppress the edema in the foot was observed when dipropionylcyclopentenone was intraperitoneally administered at 1 mg/kg. Intraperitoneal administration at 10 mg/kg or oral administration at 30 mg/kg resulted in significant suppression. In addition, optical isomers of the cyclopentenone derivatives and salts thereof exhibited similar activities.

Furthermore, other cyclopentenone derivatives or optical isomers thereof, or salts thereof exhibited similar activities.

In FIG. 6, marks * and ** represent significant differences of p<0.05 and p<0.01 as compared with the control group, respectively.

EXAMPLE 11

(1) A spleen was taken out from ddY mouse (male, 7 weeks old, purchased from Japan SLC), finely minced and suspended in RPMI-1640 medium containing 10% FCS (HyClone) to obtain a single cell suspension. The cell suspension was seeded into a plastic Petri dish and cultured at 37° C. for 2 hours in a $CO_2$ incubator to remove adhesive cells adhered to the dish. Non-adhesive cells were used as spleen lymphocytes. 200 μl of suspension of the spleen lymphocytes at a cell concentration of 2×10$^6$/ml was seeded into each well of a 96-well microtiter plate. Dipropionylcyclopentenone at a varying concentration was added to each well other than the control well. Furthermore, 5 μg of Con A (Nacalai Tesque) was added to each well. The plate was incubated at 37° C. for 1 day in a $CO_2$ incubator. After incubation, 1 μCi of $^3$H-thymidine was added to each well. After culturing for additional 1 day, the uptake into cells was measured using a liquid scintillation counter.

Figure 7:
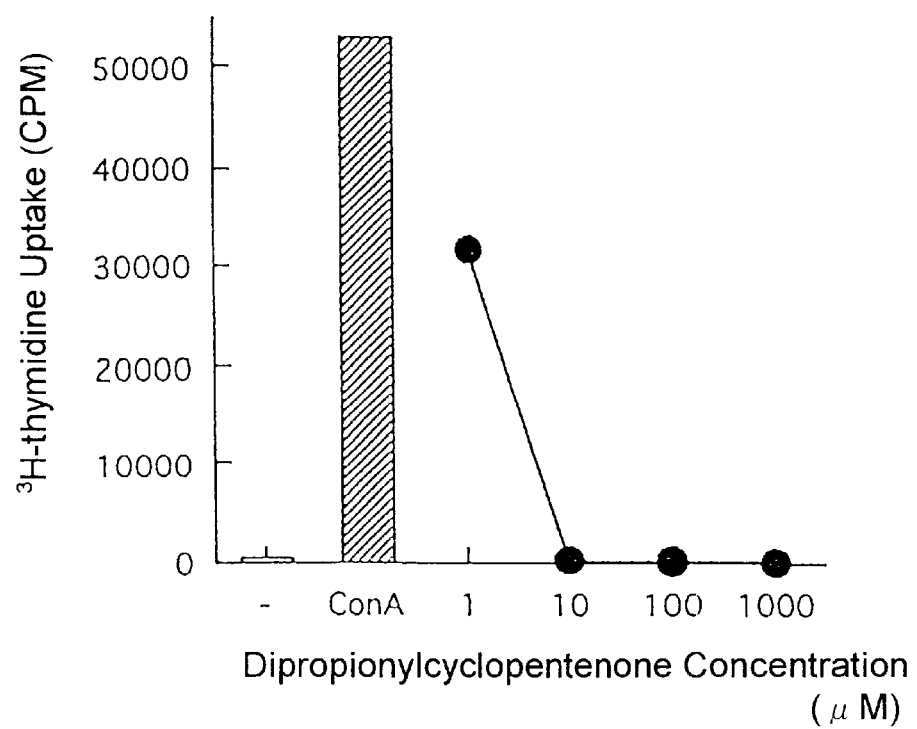
FIG. 7 illustrates the relationship between the concentration of dipropionylcyclopentenone and the amount $^3$H-thymidine uptake.

The results are shown in FIG. 7. FIG. 7 illustrates the relationship between the concentration of dipropionylcyclopentenone and the amount of $^3$H-thymidine uptake. The horizontal axis represents dipropionylcyclopentenone concentration (μM) and the vertical axis represents the $^3$H-thymidine uptake (CPM). The open bar represents the $^3$H-thymidine uptake without stimulation. The shaded bar represents the $^3$H-thymidine uptake when cells were stimulated with Con A. As seen from FIG. 7, dipropionylcyclopentenone exhibited an inhibitory activity against the proliferation of mouse lymphocytes stimulated with a mitogen in a dose-dependent manner. The proliferation was almost completely inhibited at a concentration of 10 μM. In addition, optical isomers of the cyclopentenone derivatives and salts thereof exhibited similar activities.

Furthermore, other cyclopentenone derivatives or optical isomers thereof, or salts thereof exhibited similar activities.

(2) Spleens were taken out from a BALB/c mouse (male, 6 weeks old, purchased from Japan SLC) and a C57BL/6 mouse (male, 6 weeks old, purchased from Japan SLC) and spleen lymphocytes were obtained according to the method as described in Example 11-(1). The concentration of each of the cell suspensions was adjusted to 2×10$^6$ cell/ml, 100 μl portions from respective suspensions were mixed together and seeded into a 96-well microtiter plate. Dipropionylcyclopentenone at a varying concentration was added to the wells other than the control well, and the plate was incubated at 37° C. for 4 days in a $CO_2$ incubator. After incubation, 1 μCi of $^3$H-thymidine was added to each well, and the plate was incubated for additional 1 day. The uptake into cells was measured using a liquid scintillation counter.

Figure 8:
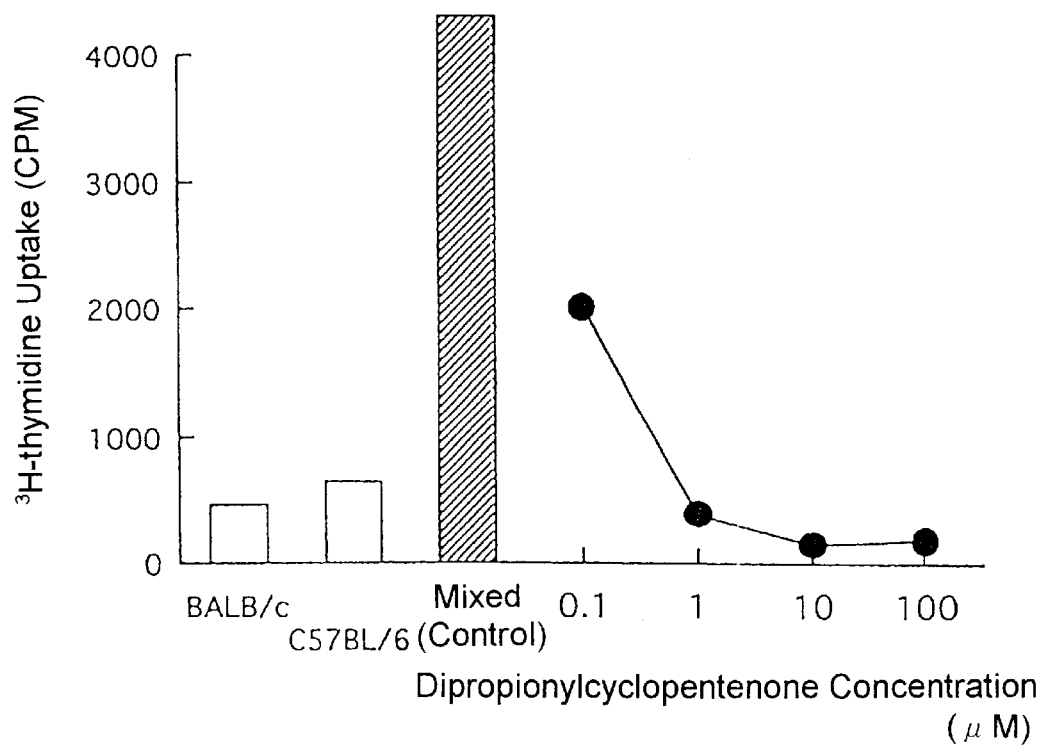
FIG. 8 illustrates the relationship between the concentration of dipropionylcyclopentenone and the amount of $^3$H-thymidine uptake.

The results are shown in FIG. 8. FIG. 8 illustrates the relationship between the concentration of dipropionylcyclopentenone and the amount of $^3$H-thymidine uptake. The horizontal axis represents the dipropionylcyclopentenone concentration (μM) and the vertical axis represents $^3$H-thymidine uptake (CPM). The open bar represents the $^3$H-thymidine uptake when cells from one of the lines were used independently. The shaded bar represents the $^3$H-thymidine uptake when cells from both of the lines were mixed together. As seen from FIG. 8, dipropionylcyclopentenone exhibited an inhibitory activity against lymphocytes activated by stimulation with an alloantigen in a dose-dependent manner. The reaction was almost completely inhibited at a concentration of 1 μM. In addition, optical isomers of the cyclopentenone derivatives and salts thereof exhibited similar activities.

Furthermore, other cyclopentenone derivatives or optical isomers thereof, or salts thereof exhibited similar activities.

EXAMPLE 12

(1) A model for endotoxin shock was constructed using CDF1 mice (8 weeks old, female, purchased from Japan SLC). Distilled water (control), or 10 mg/kg of diisopropionylcyclopentenone or diisobutyrylcyclopentenone was subcutaneously administered to a mouse. 20 μg of lipopolysaccharide (LPS; Sigma) was intraperitoneally administered to each mouse 30 minutes after the administration. Blood was collected from the mouse 1.5 hours after the administration with LPS. The amount of tumor necrosis factor (TNF)-α in a serum separated from the collected blood was measured using a commercially available ELISA kit (R&D). Each group consisted of 4 mice.

The results are shown in Table 6.

TABLE 6

| Group | Dose (mg/kg) | Amount of TNF (ng/ml) mean ± SE |
|---|---|---|
| Control | | 7.53 ± 0.48 |
| Diisopropionyl-cyclopentenone | 10 | 4.61 ± 0.57** |
| Diisobutyryl-cyclopentenone | 10 | 3.39 ± 0.33*** |

TNF-α production was significantly suppressed in the groups to which 10 mg/kg of diisopropionylcyclopentenone or diisobutyrylcyclopentenone was administered as compared with the control group to which distilled water was administered. In Table 6, marks  and * represent significant differences of p<0.01 and p<0.001 as compared with the control group, respectively. In addition, optical isomers of the cyclopentenone derivatives and salts thereof exhibited similar activities.

Furthermore, other cyclopentenone derivatives or optical isomers thereof, or salts thereof exhibited similar activities.

(2) A model for endotoxin shock was constructed by intraperitoneally administering 20 μg of LPS to a CDF1 mouse (8 weeks old, female). 30 or 100 mg/kg of dipropionylcyclopentenone or diisobutyrylcyclopentenone was orally administered 30 minutes before the administration with LPS. Blood was collected from the mouse 1.5 hours after the administration with LPS. The amount of TNF-α in a serum separated from the collected blood was measured using an ELISA kit. Each group consisted of 4 mice.

The results are shown in Table 7. The oral administration of dipropionylcyclopentenone or diisobutyrylcyclopentenone suppressed the TNF production in a dose-dependent manner as compared with the control group. In addition, optical isomers of the cyclopentenone derivatives and salts thereof exhibited similar activities.

Furthermore, other cyclopentenone derivatives or optical isomers thereof, or salts thereof exhibited similar activities.

TABLE 7

| Group | Dose (mg/kg) | TNF (ng/ml) mean ± SE |
| --- | --- | --- |
| Control | — | 5.72 ± 1.02 |
| Dipropionyl-cyclopentenone | 30 | 2.95 ± 0.14* |
|  | 100 | 1.26 ± 0.15** |
| Diisobutyryl-cyclopentenone | 30 | 3.92 ± 0.13 |
|  | 100 | 2.48 ± 0.43* |

*, **p < 0.05, 0.01 vs control.

EXAMPLE 13

(1) Mouse leukemia P-388 ($1.1 \times 10^6$ cells/mouse) was intraperitoneally administered to a 7-weeks old female DBA/2 mouse. Immediately after the administration, a single dose of 10 mg/kg dipropionylcyclopentenone was intraperitoneally administered. On the other hand, saline was intraperitoneally administered to a control group in a similar manner. Survival number of mice, average days of survival and prolongation rate were calculated for 2 groups each consisting of 8 mice.

As a result, the average days of survival were 10.1 days for the control group. The average days of survival were 13.9 days for the group administered with dipropionylcyclopentenone. The prolongation rate was calculated as 137.0%. Thus, a significant prolongation effect was observed.

Similarly, examination was carried out using a system of Meth A tumor cells: BALB/c mouse. As a result, the average days of survival were 13.4 days for the control group. The average days of survival were 16.9 days for the group administered with dipropionylcyclopentenone. The prolongation rate was calculated as 126.2%, indicating a significant prolongation effect.

In addition, optical isomers of the cyclopentenone derivatives and salts thereof exhibited similar activities.

Furthermore, other cyclopentenone derivatives or optical isomers thereof, or salts thereof exhibited similar activities.

(2) Mouse solid tumor Meth A ($2 \times 10^6$ cells/mouse) was subcutaneously injected into a back of a 8-weeks old female BALB/c mouse. Subsequently, dipropionylcyclopentenone was subcutaneously injected at the same site for successive 5 days. Saline was subcutaneously injected to a control group in a similar manner. Each group consisted of 8 mice.

After 2 weeks, the cancerous tissue formed in the back of the mouse was taken out and the weight of the tissue was measured.

The results are shown in Table 8. The average weight of cancer was 0.61 g for the control group. The average weight was 0.05 g for the group administered with dipropionylcyclopentenone. The inhibition rate was calculated as 92.3%. No cancerous tissue was formed in 5 out of 8 mice. In addition, optical isomers of the cyclopentenone derivatives and salts thereof exhibited similar activities.

Furthermore, other cyclopentenone derivatives or optical isomers thereof, or salts thereof exhibited similar activities.

TABLE 8

| Group | Weight of cancer (g) mean ± SE | Inhibition rate (%) |
| --- | --- | --- |
| Control | 0.61 ± 0.20 | — |
| Dipropionyl-cyclopentenone | 0.05 ± 0.08 | 92.3 |

(3) The carcinostatic activities of dipropionylcyclopentenone and diisobutyrylcyclopentenone against various ascitic cancers were examined using two types of cancer cells, Ehrlich ascites carcinoma (EAC) and Meth A, administered intraperitoneally or orally at a varying dose. The number of intraperitoneally transplanted cells and the host animals are shown in Table 9.

TABLE 9

| Cancer cells | Mouse | Number of transplanted cells |
| --- | --- | --- |
| EAC | ddY (female, 5 weeks old) | $1.2 \times 10^6$ |
| Meth A | BALB/c (female, 7 weeks old) | $2.0 \times 10^6$ |

Dipropionylcyclopentenone or diisobutyrylcyclopentenone was intraperitoneally or orally administered for 5 successive days from the day after the transplantation with cancer cells. Injectable distilled water was administered to a control group in a similar manner. Average days of survival, prolongation rate and 30-day survival number were calculated for groups each consisting of 8 mice.

The results are shown in Tables 10 to 13. Table 10 shows the prolongation effects when the respective test substances were intraperitoneally administered to mice transplanted with EAC. Table 11 shows the prolongation effect when the respective test substances were intraperitoneally administered to mice transplanted with Meth A. Table 12 shows the prolongation effects when the respective test substances were orally administered to mice transplanted with EAC. Table 13 shows the prolongation effect when the respective test substances were orally administered to mice transplanted with Meth A.

Dipropionylcyclopentenone and diisobutyrylcyclopentenone exhibited excellent prolongation effects in the mice transplanted with EAC. In particular, 30-day survival mice were observed in both of the groups of intraperitoneal administration. Dipropionylcyclopentenone exhibited strong effects even if it was orally administered.

Furthermore, prolongation effect was observed for the group treated by intraperitoneal administration among the mice transplanted with Meth A. 30-day survival mice were observed in the group of oral administration with dipropionylcyclopentenone.

In addition, optical isomers of the cyclopentenone and salts thereof exhibited similar activities.

Furthermore, other cyclopentenone derivatives or optical isomers thereof, or salts thereof exhibited similar activities.

TABLE 10

| Group | Dose (mg/kg) | Average days of survival (days) | Prolongation rate (%) | 30-day survival number |
|---|---|---|---|---|
| Control | | 12.5 | 100 | 0 |
| Dipropionyl-cyclopentenone | 10 | 28.1 | >225 | 6 |
| Diisobutyryl-cyclopentenone | 30 | 25.3 | >202 | 3 |
| | 10 | 17.0 | 136 | 0 |

TABLE 11

| Group | Dose (mg/kg) | Average days of survival (days) | Prolongation rate (%) | 30-day survival number |
|---|---|---|---|---|
| Control | | 11.8 | 100 | 0 |
| Dipropionyl-cyclopentenone | 10 | 20.5 | 174 | 0 |
| Diisobutyryl-cyclopentenone | 10 | 15.5 | 132 | 0 |

TABLE 12

| Group | Dose (mg/kg) | Average days of survival (days) | Prolongation rate (%) | 30-day survival number |
|---|---|---|---|---|
| Control | | 12.5 | 100 | 0 |
| Dipropionyl-cyclopentenone | 30 | 24.1 | >193 | 4 |
| Diisobutyryl-cyclopentenone | 100 | 20.9 | 167 | 0 |
| | 30 | 15.1 | 121 | 0 |

TABLE 13

| Group | Dose (mg/kg) | Average days of survival (days) | Prolongation rate (%) | 30-day survival number |
|---|---|---|---|---|
| Control | | 11.8 | 100 | 0 |
| Dipropionyl-cyclopentenone | 30 | 17.3 | >147 | 2 |

EXAMPLE 14

Injectable Preparation (1) Diisobutyrylcyclopentenone, dipropionylcyclopentenone or dimethoxycyclopentenone was added to saline at a concentration of 1% to prepare injectable preparations.

(2) Dimethylfumarylcyclopentenone or dimethylmaleylcyclopentenone and glycyrrhizic acid was added to saline at concentrations of 0.5% and 0.1%, respectively, to prepare injectable preparations.

EXAMPLE 15

Tablet (1) Tablets each containing 100 mg of diisobutyrylcyclopentenone or dipropionylcyclopentenone and a suitable amount of crystallite cellulose were prepared and sugar-coated.

(2) Tablets each containing 0.1 mg of dimethylfumarylcyclopentenone, 10 mg of glycyrrhizic acid dipotassium salt and a suitable amount of crystallite cellulose were prepared and sugar-coated.

As described above, the present invention provides cyclopentenone derivatives or optical isomers thereof, or salts thereof having physiological activities such as an immunoregulatory activity, an anti-inflammatory activity, an activity of inhibiting tumor necrosis factor production and an anti-fungal activity. Pharmaceutical compositions containing these compounds as their active ingredients are useful for maintaining homeostasis in a living body as pharmaceutical compositions for treating or preventing a disease that requires immunoregulation for its treatment or prevention, a disease that requires suppression of inflammation for its treatment or prevention, a disease that requires inhibition of tumor necrosis factor production for its treatment or prevention, a disease that requires growth inhibition of pathological microorganism for its treatment or prevention and the like.

What is claimed is:

1. A method for treating or preventing a disease that requires immunoregulation for its treatment or prevention, a disease that requires suppression of inflammation for its treatment or prevention, a disease that requires inhibition of tumor necrosis factor production for its treatment or prevention, a disease that requires inhibition of a fungus for its treatment or prevention, a disease that requires inhibition of cell adhesion for its treatment or prevention, a disease that requires activation of NK cells for its treatment or prevention or a disease that requires induction of heat shock protein for its treatment or prevention, the method comprising administering to a subject in need thereof a pharmaceutical composition which contains as an active ingredient, in an amount sufficient therefor, of at least one compound of formula (I):

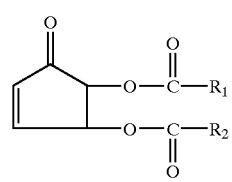

[I]

wherein $R_1$ and $R_2$ may be identical or different from each other, and are hydrogen, an aliphatic group, an aromatic group or an aromatic aliphatic group, or an optical isomer or salt thereof.

2. The method according to claim 1, wherein $R_1$ and $R_2$ are identical or different from each other, and are hydrogen, a linear or branched C1–30 alkyl group, a linear or branched C2–30 alkenyl group, a C6–10 aryl group or a C1–30 alkyl C6–10 aryl group, optionally substituted with at least one substituent selected from the group consisting of a C1–30 alkyl group, a C1–4 alkoxy group, a C2–5 alkoxycarbonyl group, an amino group, a nitro group, an oxo group, a hydroxyl group, a thiol group, a sulfate group and a halogen.

3. The method according to claim 1, wherein the cyclopentenone derivative of formula (I) is diacetylcyclopentenone, dipropionylcyclopentenone, dibutyrylcyclopentenone, diisobutyrylcyclopentenone, divalerylcyclopentenone, dihexanoylcyclopentenone, dioctanoylcyclopentenone, didecanoylcyclopentenone, dimyristoylcyclopentenone, dimethoxyacetylcyclopentenone, dimethylfumarylcyclopentenone, dimethylmaleylcyclopentenone, di-2-hexenoylcyclopentenone, di-3-octenoylcyclopentenone or dibenzoylcyclopentenone.

4. The method according to claim 1, wherein said sufficient amount is an immunoregulatory-effective amount, a tumor necrosis factor production inhibiting-effective amount, an anti-fungal effective amount, a cell adhesion inhibiting-effective amount, an NK cell activating-effective amount, or a heat shock protein-inducing amount.

* * * * *